United States Patent
Rigo et al.

(10) Patent No.: US 10,010,880 B2
(45) Date of Patent: *Jul. 3, 2018

(54) LIGANDS OF THE BENZO [H] QUINOLINE CLASS AND TRANSITION METAL COMPLEXES CONTAINING THEM AND USE OF SAID COMPLEXES AS CATALYSTS

(71) Applicant: UNIVERSITA' DEGLI STUDI DI UDINE, Udine (IT)

(72) Inventors: Pierluigi Rigo, Udine (IT); Walter Baratta, Udine (IT); Katia Siega, Tarvisio (IT); Giorgio Adolfo Chelucci, Sassari (IT); Maurizio Ballico, Udine (IT); Santo Magnolia, Udine (IT)

(73) Assignee: UNIVERSITA' DEGLI STUDI DI UDINE (IT)

(*) Notice: Subject to any disclaimer, the term of this patent is extended or adjusted under 35 U.S.C. 154(b) by 0 days.

This patent is subject to a terminal disclaimer.

(21) Appl. No.: 15/071,883

(22) Filed: Mar. 16, 2016

(65) Prior Publication Data
US 2016/0279624 A1    Sep. 29, 2016

Related U.S. Application Data

(60) Continuation of application No. 14/083,710, filed on Nov. 19, 2013, now Pat. No. 9,409,867, which is a division of application No. 12/452,553, filed as application No. PCT/EP2008/059060 on Jul. 11, 2008, now Pat. No. 8,614,322.

(30) Foreign Application Priority Data

Jul. 11, 2007   (IT) .............................. PD2007A0237

(51) Int. Cl.

| C07F 15/00 | (2006.01) |
|---|---|
| C07D 221/06 | (2006.01) |
| B01J 31/24 | (2006.01) |
| C07D 221/10 | (2006.01) |
| C07C 1/22 | (2006.01) |
| C07C 29/14 | (2006.01) |
| C07C 29/143 | (2006.01) |
| B01J 31/22 | (2006.01) |

(52) U.S. Cl.
CPC ....... *B01J 31/2409* (2013.01); *B01J 31/2295* (2013.01); *C07C 1/22* (2013.01); *C07C 29/14* (2013.01); *C07C 29/143* (2013.01); *C07D 221/10* (2013.01); *C07F 15/002* (2013.01); *C07F 15/0026* (2013.01); *C07F 15/0046* (2013.01); *C07F 15/0053* (2013.01); *B01J 2231/643* (2013.01); *B01J 2531/821* (2013.01); *B01J 2531/825* (2013.01)

(58) Field of Classification Search
None
See application file for complete search history.

(56) References Cited

U.S. PATENT DOCUMENTS

| 6,184,381 B1 | 2/2001 | Ikariya et al. |
|---|---|---|
| 6,372,931 B1 | 4/2002 | Blacker et al. |
| 6,451,727 B2 | 9/2002 | Zhang |
| 6,545,188 B2 | 4/2003 | Blacker et al. |
| 6,878,852 B2 | 4/2005 | Rautenstrauch et al. |
| 7,638,628 B2 | 12/2009 | Baratta et al. |
| 8,614,322 B2* | 12/2013 | Rigo ................... C07D 221/10 546/10 |

FOREIGN PATENT DOCUMENTS

| JP | H06-047235 | 7/1991 |
|---|---|---|
| WO | 2005105819 A1 | 11/2005 |

OTHER PUBLICATIONS

Crepy, K. et al. New P-Chirogenic Phosphine Ligands and Their Use in Catalytic Asymmetric Reactions. Top. Curr. Chem. 2003, vol. 229, p. 4.*
Suarez, M. et al. Triruthenium and Triosmium Carbonyl Cluster Complexes Containing Bridging Ligands Derived from 2-amino-7,8-benzoquinoline. Organometallics. 2002, vol. 21, p. 5055.
Cabeza et al. Triruthenium and Triosmium Carbonyl Cluster Complexes Containing Bridging Ligands Derived from 2-amino-7,8-benzoquinoline. Organometallics. 2002, vol. 21, p. 5055.
Baratta, W. et al. Ruthenium(II) Terdentate CNN Complexes: Superlative Catalysts for the Hydrogen-Transfer Reduction of Ketones by Reversible Insertion of a Carbonyl Group into the Ru—H Bond. Angew. Chem. Int. Ed.. 2005, vol. 44, p. 6214.
Engbersen, JFJ. et al. Synthesis of 2-Aminomethy1-1,10-phenanthroline. A new Chelating Agent and Versatile Synthon for other Chelating Compounds. J. Heterocyclic Chem., 1986, vol. 23, p. 989.
Carey, FA. Organic Chemistry 6th Ed. McGraw Hill. 2006, chapter 2, p. 63.
Albrecht, G. van Koten, Angew. Chem. Int. Ed. 2001, 40, pp. 3750-3781.
M. E. van der Boom, D. Milstein, Chem. Rev. 2003, 103, pp. 1759-1792.
J. T. Singleton, Tetrahedron 2003, 59, pp. 1837-1857.
W. Baratta, P. Da Ros, A. Del Zotto, A. Sechi, E Zangrando, P. Rigo, Angew. Chem. Int. Ed., 2004, 43, pp. 3584-3588.
J.B. Sortais,V. Ritleng, A. Voelklin, A. Holuigue, H. Smail, L. Barloy, C. Sirlin, G.K.M. Verzijl, J. A. F. Boogers, A.H.M. de Vries, J. G. de Vries, M. Pfeffer, Organic Letters, 2005, vol. 7, No. 7, pp. 1247-1250.
J.B. Sortais, L. Barloy, C. Sirlin, A.H.M. de Vries, J. G. de Vries, M. Pfeffer, Pure Appl. Chem., 2006, 78, pp. 457-462.

(Continued)

*Primary Examiner* — Andrew D Kosar
*Assistant Examiner* — Ben S Michelson
(74) *Attorney, Agent, or Firm* — Lisa A. Chiarini; Reed Smith LLP

(57) ABSTRACT

A new class of ligands derived from benzo[h]quinoline are described and these ligands are used to prepare several novel transition metal complexes. The complexes are preferably of the group VIII transition metals iron, ruthenium or osmium, with the benzo[h]quinolone ligands acting as tridentate ligands. The complexes described are proved to be very active catalysts for the reduction of ketones and aldehydes to alcohols, via hydrogen transfer and hydrogenation reactions. These compounds hence can be usefully employed as catalysts in said reduction reactions.

28 Claims, 1 Drawing Sheet

(56) References Cited

OTHER PUBLICATIONS

W. Baratta, G. Chelucci, S. Gladiali, K. Siega, M. Toniutti, M. Zanette, E. Zangrando, P. Rigo, Angew. Chem. Int. Ed., 2005, 44, pp. 6214-6219.
F. Fache, E. Schulz, M. L. Tommasino, M. Lemaire, Chem. Rev., 2000, 100, pp. 2159-2231.
R. Noyori, T. Ohkuma, Angew. Chem., Int. Ed., Engl. 2001, 40, pp. 40-73.
S.E. Clapham, A. Hadzovic, R.H. Morris, Coord. Chem. Rev., 2004, 248, pp. 2201-2237.
W. Baratta, E. Herdtweck, K.Siega, M. Toniutti, P. Rigo, Organometallics 2005, 24, pp. 1660-1669.
T. Ohkuma, C. A. Sandoval,R. Srinivasan, Q. Lin, Y. Wei, K. Muniz, R. Noyori, J. Am.Chem. Soc. 2005, 127, pp. 8288-8289.
F. Naud, C. Malan, F. Spindler, C. Ruggerberg, A. T. Schimdt, H-U Blaser, Adv. Synth. Catal. 2006, 348, pp. 47-50.
R. Noyori, Asymmetric Catalysis in Organic Synthesis, Ed. R. Noyori, 1994, pp. 56-82.
T. Ohkuma, H.Ooka, T. Ikariya, R. Noyori, J. Am. Chem. Soc. 1995, 117, pp. 10417-10418.
K. V. L Crepy, T. Imamoto, Adv. Synth. Catal. 2003, 345, pp. 79-101.
V. Rautenstrauch, X. Hoang-Cong, R. Churland, K. Abdur-Rashid, R.H. Morris, Chem. Eur. J. 2003, 9, pp. 4954-4967.
H. A. McManus, P. J. Guiry, Chem. Rev. 2004, 104, pp. 4151-4202.
G. Zassinovich, G. Mestroni, S. Gladiali, Chem. Rev. 1992, 92, pp. 1051-1069.
R. Noyori, S. Hashiguchi, Acc. Chem. Res. 1997, vol. 30, No. 2, pp. 97-102.
J.-E. Backvall, J. Organomet. Chem. 2002, 652, pp. 105-111.
M. J. Palmer, M. Wills, Tetrahedron: Asymmetry 1999, 10, pp. 2045-2061.
J. S. M. Samec, J. E Backvall, P. G. Andersson, P. Brandt, Chem. Soc. Rev. 2006, 35, pp. 237-248.
S. Gladiali, E. Alberico, Chem. Soc. Rev. 2006, 35, pp. 226-236.
A. C. Hillier, H. M. Lee, E. D. Stevens, S. P, Nolan, Organometallics 2001, 20, pp. 4246-4252.
K.-J. Haack, S. Hashiguchi, A. Fujii, T. Ikariya, R. Noyori, Angew. Chem. Int. Ed. Engl. 1997, 36, No. 3, pp. 285-288.
K. Everaere, A. Mortreaux, J.-F. Carpentier, Adv. Synth. Catal. 2003, 345, pp. 67-77.
T. Ikariya, K. Murata, R. Noyori, Org. Biomol. Chem. 2006, 4, pp. 393-406.
J.-X. Gao, T. Ikarya, R. Noyori, Organometallics, 1996, 15, pp. 1087-1089.
Y. Jiang, Q. Jiang, X, Zhang, J. Am. Chem. Soc. 1998, 120, pp. 3817-3818.
Y. Nishibayashi, I. Takei, S. Uemura, M. Hidai, Organometallics 1999, 18, pp. 2291-2293.
W. Baratta, M. Bosco, G. Chelucci, A. Del Zotto, K. Siega, M. Toniutti, E. Zangrando, P. Rigo, Organometallics 2006, 25, pp. 4611-4620.
P. Dani, T. Karlen, R. A. Gossage, S. Gladiali, G. van Koten, Angew. Chem. Int. Ed. Engl. 2000, 39, No. 4, pp. 743-745.
M. Gagliardo, P. A. Chase, S. Brouwer, G. P. M. van Klink, G. van Koten, Organometallics, 2007, 26, pp. 2219-2227.
H. Yang, M. Alvarez, N. Lugan, R. Mathieu, J. Chem. Soc., Chem. Commun. 1995, pp. 1721-1722.
H. Yang, M. Alvarez-Gressier, N. Lugan, R. Mathieu, Organometallics 1997, 16, pp. 1401-1409.
C. Thoumazet, M. Melaimi, L. Ricard, F. Mathey, P. Le Floch, Organometallics 2003, 22, pp. 1580-1581.
R.H.Morris in The Handbook of Homogeneous Hydrogenation, 2007, 1, 45—Eds. J. G. de Vries, C. J. Elsevier—Wiley-VCH, Weinheim.
G. Chelucci, S. Medici, A. Saba, Tetrahedron: Asymmetry 1999, 10, pp. 543-550.
Cappelli et al., J. Med. Chem. 1998, 41, pp. 728-741.
P. S. Hallmann, T. A. Stephenson, G. Wilkinson, Checked by Richard Holm, Inorg. Synth. 1970, 12, pp. 237-240.
C. W. Jung, P. E. Garrou, P. R. Hoffman, K. G. Caulton, Inorg. Chem. 1984, 23, pp. 726-729.
Elliott, G. P.; McAuley, N. M.; Roper, W. R., Inorg. Synth. 1989, 26, pp. 184-185.
IUPAC Compendium of Chemical Terminology, Gold Book, version 2.3, 2011, pp. 57, 109-110, and 694.
X. Zhang, W, Tang, "New Chiral Phosphorus Ligands for Enantioselective Hydrogenation", Chem. Rev. 2003, 103, pp. 3029-3069.
T. Saito, H. Shimizu, I. Nagasaki, "Recent advances in biaryl-type bisphosphine ligands", Tetrahedron 61 (2005), pp. 5405-5432.
J.C. Carretero, R. G. Arrayas, J. Adrio, "Recent Applications of Chiral Ferrocene Ligands in Asymmetric Catalysis", Angew. Chem. Int. Ed., 2006, 45, pp. 7674-7715.
International Search Report, dated Jan. 2009.
Written Opinion of the International Searching Authority, dated Sep. 2009.
International Preliminary Report on Patentability (IPRP), dated Jan. 2009.
Zimmer, H et al. "Kondensierte Imidazole; Versuche zur Synthese des 13,16- und 14,16-Diazasterin-Gerustes," Chimia, Aarau, CH, vol. 26, No. 3, Mar. 1972, pp. 131-133, XP-002101985.
Baratta, W. et al., "Ruthenium(II) Terdentate CNN Complexes: Superlative Catalysts for the Hydrogen-Transfer Reduction of Ketones by Reversible Insertion of a Carbonyl Group into the Ru—H Bond," Angewandte Chemie (International Ed. In English) Sep. 2005, vol. 44, No. 38, pp. 6214-6219, XP-002510286.
Baratta, W. et al., "New Benzo(h)quinoline-Based Ligands and their Pincer Ru and Os Complexes for Efficient catalytic Transfer Hydrogenation of Carbonyl Compounds," Chemistry (Weinheim an Der Bergstrasse, Germany), vol. 14, No. 30, Sep. 2008, pp. 9148-9160, XP-002510333.
Johnstone, RA. et al. Heterogeneous Catalytic Transfer Hydrogenation and Its Relation to Other Methods for Reduction of Organic Compounds. Chem. Rev. 1985, vol. 85, p. 141.
Dorwold, FZ. Side Reactions in Organic Synthesis. Wiley. 2005, preface.

\* cited by examiner

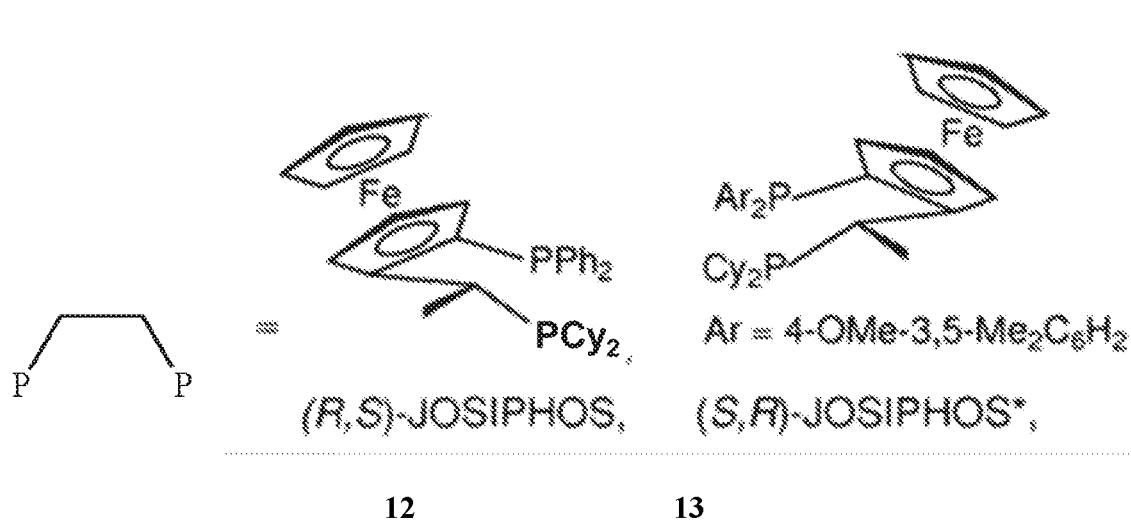
12         13
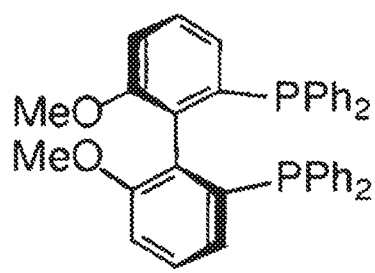
(S,S)-SKEWPHOS,
14
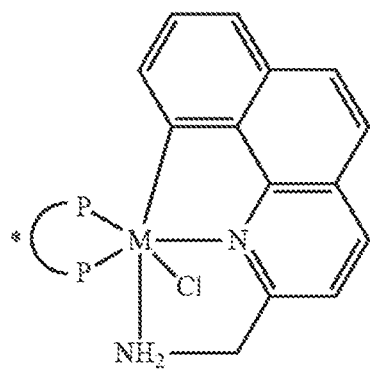
(S)-MeO-BIPHEP
15

LIGANDS OF THE BENZO [H] QUINOLINE CLASS AND TRANSITION METAL COMPLEXES CONTAINING THEM AND USE OF SAID COMPLEXES AS CATALYSTS

CROSS REFERENCE

This application is a continuation application of divisional patent application U.S. Ser. No. 14/083,710, filed Nov. 19, 2013 which is a divisional of U.S. Ser. No. 12/452,553, filed Jan. 8, 2010, now U.S. Pat. No. 8,614,322 which is a § 371(c) national phase filing of PCT/EP2008/059060, filed Jul. 11, 2008, which claims priority to Application No. PD2007A0000237, filed Jul. 11, 2007, the entire contents of each of which are incorporated herein by reference.

FIELD OF THE INVENTION

The invention relates to new tridentate ligands derived from benzo[h]quinolone and to new complexes of transition metals, in particular group VIII transition metals selected from iron, ruthenium and osmium obtained therewith. The invention relates also to methods for preparing the ligands and the relative complexes as well as to the use of the complexes, isolated or prepared in situ, as catalysts of ketone, aldehyde and imine reduction reactions either by hydrogen transfer or with hydrogen gas.

STATE OF THE ART

In recent years cyclometalated transition metal complexes containing either tridentate (PCP, NCN, CNN) (M. Albrecht, G. van Koten, *Angew. Chem. Int. Ed.* 2001, 40, 3750; M. E. van der Boom, D. Milstein, *Chem. Rev.* 2003, 103, 1759; J. T. Singleton, *Tetrahedron* 2003, 59, 1837) or bidentate (PC, NC) cyclometalated ligands (W. Baratta, P. Da Ros, A. Del Zotto, A. Sechi, E. Zangrando, P. Rigo, *Angew. Chem. Int. Ed.*, 2004, 43, 3584; I. B. Sortais, V. Ritleng, A. Voelklin, A. Holuigue, H. Small, L. Batyol, C. Sirlin, G. K. M. Verzijl, A. H. M. de Vries, M. Pfeffer, *Org. Lett,* 2005, 7, 1247) have found various applications in organometallic chemistry and in homogeneous catalysis. The interest in catalysis for these systems derives from the fact that they generally have a high degree of thermal stability and that the presence of a metal-carbon a covalent bond hinders the detaching of the ligand from the metal. For example cyclometalated Ru complexes, with either bidentate CN ligands (J. B. Sortais, L. Bariol, C. Sirlin, A. H. M. de Vries, J. G. de Vries, M. Pfeffer, *Pure Appl. Chem,* 2006, 78, 475) or tridentate CNN ligands (W. Baratta, G. Chelucci, S. Gladiali, K Siega, M Toniutti, M Zanette, E. Zangrando, P. Rigo, *Angew. Chem. Int. Ed.* 2005, 44, 6214), have been used with good results as catalytic precursors in hydrogen transfer reactions. It is also to be noted that bidentate N-donor ligands have found a number of applications over recent decades in the synthesis of various types of catalytic systems based on transition metals either alone or in combination with other ancillary ligands such as phosphines and arenes (M. Lemaire et al., *Chem. Rev.,* 2000, 100, 2159). Hence Ru/diphosphine/diamine systems, with diamines of the type $H_2N-Q-NH_2$, are excellent catalysts for the selective homogeneous hydrogenation of various types of ketones (R. Noyori, T. Ohkuma, *Angew. Chem., Mt. Ed. Engl.* 2001, 40, 40; R. H. Morris et al., *Coord. Chem. Rev.* 2004, 248, 2201), whereas when the bidentate N-donor ligand is of the amino-pyridine type, [$RuCl_2$(diphosphine)(2-aminomethylpyridine)], these systems are particularly active as catalysts in the reduction of carbonyl compounds by hydrogen transfer in 2-propanol (W. Baratta, E. Herdtweck, K. Siega, M. Toniutti, P. Rigo, *Organometallics* 2005, 24, 1660; W. Baratta, K. Siega. M. Toniutti, P. Rigo, WO 200511058191). The catalytic activity in hydrogen transfer increases further by using ligands, such as 6-aryl-2-(aminomethyl)pyridine, in which a group able to give cyclometalation reactions is linked to the 2-aminomethylpyridine backbone (W. Baratta, G. Chelucci, S. Gladiali, K. Siega, M Toniutti, M. Zanette, E. Zangrando, P. Rigo, *Angew. Chem. Int. Ed.* 2005, 44, 6214).

The reduction of carbonyl compounds such as ketones and aldehydes is a reaction of wide-ranging applicative interest that has led in the recent years to an intense research activity. In this respect, as well as biocatalytic reduction methods and methods based on the use of metal hydrides such as LiAlH4, two additional and different hydrogenation methods have been developed:

1) reduction with molecular hydrogen using catalytic systems based on transition metals;
2) catalytic reduction by hydrogen transfer, using formic acid or 2-propanol as hydrogen donors.

Good results have been obtained with both methods using in particular systems based on ruthenium(II) complexes containing various ligand types. From an industrial viewpoint both technologies present advantages and disadvantages. In this respect hydrogenation reactions of carbonyl compounds with hydrogen gas are generally carried out under pressure, which can be a source of risk and requires dedicated plants, though with the advantage of having highly active catalytic systems which operate at moderate temperatures. In processes based on transfer reactions, 2-propanol is normally used as both the hydrogen source and reaction solvent, and presents the advantages of having a low boiling point, low toxicity and low environmental impact. Due to its simplicity of operation and the good results that it can give, catalytic hydrogen transfer is a useful alternative to reduction with hydrogen primarily for small and medium scale reactions. It should be noted, however, that catalytic systems available for hydrogen transfer are not generally highly active and this entails long reaction times and low plant utilization, in addition to the risk of catalyst deactivation and decomposition over time.

Also of note is that, with rare exceptions, the catalysts active in hydrogen transfer are poorly active in hydrogenation and vice-versa (T. Ohkuma, C. A. Sandoval, R. Srinivasan, Q. Lin, Y. Wei, K. MuCiz, R. Noyori, *J. Am. Chem. Soc.* 2005, 127, 8288; F. Naud, C. Malan, F. Spindler, C. Ruggerberg, A. T. Schimdt, H-U Blaser, *Adv. Synth. Catal.* 2006, 348, 47).

Hydrogenation Reactions

For reduction with molecular hydrogen, catalytic systems based on various transition metals (Ir, Rh, Pd, Ni) have been used: but particular attention has been concentrated on ruthenium derivatives. Compounds of the type [$RuCl_2$(phosphine)$_2$(1,2-diamine)] and [$RuCl_2$(diphosphine)(1,2-diamine)] in basic media, are excellent catalysts for the selective hydrogenation, in homogeneous phase, of various types of ketones. In addition, with a suitable combination of chiral diphosphines and diamines, enantioselcctive hydrogenation of carbonyl compounds can be achieved with the formation of optically active alcohols with high enantiomeric excesses. The reactions are generally carried out with hydrogen under pressure and moderate temperatures (R. Noyori, Asymmetric Catalysis in Organic Synthesis, Ed. R. Noyori, 1994, pp. 56-82; T. Ohkuma, H. Ooka, T. Ikariya, R. Nayori, *J. Am. Chem., Soc.* 1995, 117, 10417; R. Noyori, Ohkuma, *Angew. Chem., Int. Ed. Engl.* 2001, 40, 40; K. V.

L. Crepy, T. Imamoto, *Adv. Synth. Catal.* 2003, 345, 79; R. H. Morris et al., *Coord. Chem. Rev.* 2004, 248, 2201). It is to be noted that complexes containing bidentate ligands of amine-pyridine type, such as [RuCl$_2$(diphosphine)(2-aminomethylpyridine)], can catalyse, depending on the diphosphine and solvent, both the hydrogenation reaction and hydrogen transfer reaction (W. Baratta, E. Herdtweck, K. Siega, M. Toniutti, P. Rigo, *Organometallics* 2005, 24, 1660; T. Ohkuma, C. A. Sandoval, R. Srinivasan, Q. Lin, Y. Wei, K. Muciz, R. Noyori, *J. Am. Chem. Soc.* 2005, 127, 8288). As well as with Ru/diphosphine/diamine systems, interesting results have also been obtained in catalytic hydrogenation with ruthenium complexes containing tetradentate diamino-diphosphine and diimino-diphosphine ligands (R. H. Morris et al., *Chem., Eur. J.* 2003, 9, 4954; V. Rautenstrauch et al., U.S. Pat. No. 6,878,852) and with a series of ruthenium compounds with ligands of phosphino-oxazoline type (H. A. McManus, P. J. Guiry, *Chem. Rev.* 2004, 104, 4151; T. Naud, et al., *Adv. Synth. Catal.* 2006, 348, 47).

Hydrogen Transfer

In transfer reductions of carbonyl compounds, 2-propanol, which is also the reaction solvent, or a formic acid/triethylamine mixture, are normally used as hydrogen source (G. Zassinovich, G. Mestroni, S. Gladiali, *Chem. Rev.* 1992, 92, 1051; R. Noyori, S. Hashiguchi, *Acc. Chem. Res.* 1997, 30, 97; J. E. Bäckvall, *J. Organomet. Chem.* 2002, 662, 105; M. J. Palmer, M. Wills, *Tetrahedron: Asymmetry* 1999, 10, 2045; J. S. M. Samec, J. E. Bäckvall, P. G. Andersson, P. Brandt, *Chem. Soc. Rev.* 2006, 35, 237; S. Gladiali, E. Alberico, *Chem. Soc. Rev.* 2006, 35, 226).

Transition metal based catalysts such as rhodium and iridium have been used (M. J. Palmer, M. Wills, *Tetrahedron. Asymmetry* 1999, 10, 2045; A. J. Blazer, B. J. Mellor U.S. Pat. No. 6,372,931 and U.S. Pat. No. 6,545,188; A. C. Hillier, H. M. Lee, E. D. Stevens, S. P. Nolan. *Organometallics* 2001, 20, 4246; J. Bäckvall, *J. Organomet. Chem.* 2002, 652, 105), but the most interesting results for the enantioselective reduction of ketones have been achieved with ruthenium derivatives. These include in particular arene-ruthenium complexes with diamine or β-aminoalcohol ligands (K.-J. Haack, S. Hashiguchi, A. Fujii, T. Ikariya, R. Noyori, *Angew. Chem. Int. Ed. Engl.* 1997, 36, 285; T. Ikariya S. Hashiguchi, J. Takehara, N. Uematsu, K Matsurnara, R. Noyori, A. Fujii, U.S. Pat. No. 6,184,381; K. Everaere, A. Mortreaux, J. Carpentier, *Adv. Synth. Catal.* 2003, 345, 67; T. Ikariya, K. Murata, R. Noyori, *Org. Binmol. Chem.* 2006, 4, 393), complexes with tetradentate ligands of diphosphine-diamine and diphosphinc-diimine type (J.-X. Gao, T. Ikariya, R. Noyori, *Organometallics,* 1996, 15, 1087), complexes with oxazoline ligands (Y. Jiang, Q. Jiang, X. Zhang, *J. Am. Chem. Soc.* 1998, 120, 3817; X. Zhang, U.S. Pat. No. 6,451,727) and with oxazoline ferrocenylphosphine ligands (Y. Nishibayashi, I. Takei, S. Uemura, M. Hidai, *Organometallics* 1999, 18, 2291). Furthermore, with the 2-aminomethylpyridine ligand, complexes of the type [RuCl$_2$(P$_2$)(2-aminomethylpyridine)] (P phosphorus atoms of mono or bidentate phosphines) have been obtained, having very high catalytic activities with TOF values (turnover frequency=number of moles of ketone converted to alcohol per mole of catalyst per hour at 50% conversion) able to attain $10^5$ h$^{-1}$ (W. Baratta, E. Herdtweck, K. Siega, M. Toniutti, P. Rigo, *Organometallics* 2005, 24, 1660; W. Baratta, K. Siega, M. Toniutti, P. Rigo, WO 2005/1058191). The catalytic activity increases further using potentially tridentate ligands, such as 6-aryl-2-(aminomethyl)pyridine, containing an aryl group capable of giving cyclometalation (TOF to $10^6$ h$^{-1}$) (W. Baratta, G. Chelucci, S. Gladiali, K. Siega, M. Toniutti, M. Zanette, E. Zangrando, P. Rigo, *Angew. Chem. Int. Ed.* 2005, 44, 6214; W. Baratta, M. Bosco, G. Chelucci, A. Del Zotto, K. Siega, M. Toniutti, E. Zangrando, P. Rigo, *Organometallics* 2005, 25, 4611).

It is to be mentioned that the highly active catalytic systems for non-enantioselective reduction of ketones described by van Koten and co-workers (P. Dani, T. Karlen, R. A. Gossage, S. Gladiali, G. van Koten, *Angew. Chem., Int. Ed. Engl.* 2000, 39, 743; M. Gagliardo, P. A. Chase, S. Brouwer, G. P. M. van Klink, G. van Koten, *Organometallics,* 2007, 26, 2219) of "pincer-aryl" type of formula RuX[C$_6$H$_3$(CH$_2$PPh$_2$)$_2$-2,6](PPh$_3$) (X=Cl, CF$_3$SO$_3$), having a stable Ru—C aryl bond, and those published by Mathieu containing tridentate pyridine ligands, which exhibit TOF values of up to 90000 h$^{-1}$ for the acetophenone reduction (H. Yang, M. Alvarez. N. Lugan, R. Mathieu, *J. Chem. Soc. Chem. Commun.* 1995, 1721; H. Yang, M. Alvarez-Grassier, N. Lugan, R. Mathieu, *Organometallics* 1997, 16, 1401) even if their rapid deactivation limits their use in organic synthesis. Moreover, in a recent study, Mathey and Le Floch (C. Thoumazet, M. Melaimi, L. Ricard, F. Mathey, P. Le Floch, *Organometallics* 2003, 22, 2580) described a new arene-ruthenium catalyst containing the ligand N, P bidentate 1-(2-methylpyridine-2,5 diphenyl-phosphole, which exhibits TOF values up to $10^6$ h$^{-1}$ for a number of ketones, however the extremely long times required (several days at 90° C.) limit its practical use.

In order to make the reduction of ketones to alcohols by hydrogen transfer economically competitive, the synthesis of novel catalysts showing high activity and productivity is a fundamental target. This is particularly important if the catalytic systems can lead to enantioselective reduction, affording optically active alcohols from prochiral ketones.

To achieve the aforementioned objects the inventors have identified, a new class of compounds derived from benzo[h]quinoline, with a —CHR$_1$—NH$_2$ group in position 2 represented by the formula (I):

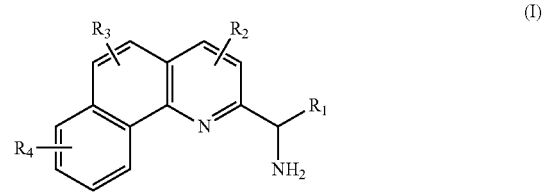

wherein:
R$_1$ is an aliphatic or an aromatic group;
R$_2$, R$_3$ and R$_4$ are equal or different each 'other and are hydrogen atoms, aliphatic or aromatic groups, halogen atoms, alkoxo groups, nitro groups, cyano groups.

The ligands of the invention, represented by the formula (Ia) (HCNN) and when deprotonated are represented by the formula (I b) (CNN)

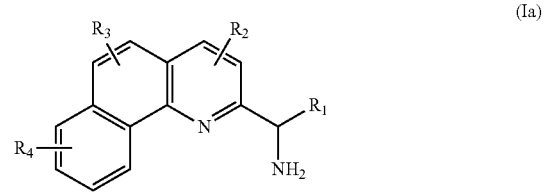

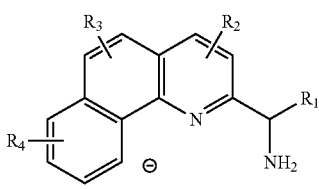

(Ib)

are a family of ligands for the synthesis of transition metal complexes to be used as catalysts in organic synthesis reactions.

The ligands of the invention with a transition metal, selected from those of group VIII consisting of iron, ruthenium, osmium, have the capability to act as tridentate ligands by coordination to the metal through the nitrogen atom of the pyridine ring and the nitrogen atom of the primary amine group. In particular said ligands with group VIII transition metals selected from iron, ruthenium and osmium give a cyclometalation reaction in position 14 with formation of a metal-carbon a bond and two 5-membered rings, forming in said manner the complexes represented by the general formula (II)

[MXL$m$L'] (II)

corresponding to the structural formula below

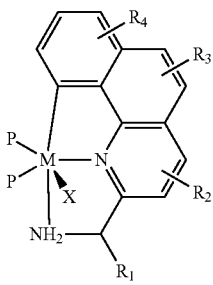

wherein:
M=a group VIII transition metal selected from iron, ruthenium and osmium;
X=a halogen, a hydrogen, an alkoxide (OR);
P=phosphorus atoms of a mono dentate or bidentate phosphine (L), or an optically active diphosphine (L);
and wherein $R_1$, $R_2$, $R_3$ and $R_4$ can have the aforementioned meanings, being the residues of the new CNN ligand of formula (Ib).

For the reduction of ketones and aldehydes to alcohols, and also of imines to amines, the preferred transition metals are ruthenium and osmium. Hence the inventors have identified, in a new class of ruthenium(II) and osmium(II) complexes with CNN type ligands in combination with mono or bidentate phosphines, the solution for obtaining, in the presence of bases, catalysts with very high catalytic activity to be used for reduction of carbonyl compounds both in hydrogen transfer reactions in 2-propanol and in hydrogenation reactions with molecular hydrogen, with the possibility of also achieving enantioselective synthesis by suitable combination with chiral phosphines.

It is to be noted that few examples of the utilization of osmium derivatives as catalysts in reduction reactions of carbonyl compounds have been reported, probably because they are more expensive and have in general a lower activity than the corresponding ruthenium derivatives (R. H. Morris in *The Handbook of Homogeneous Hydrogenation*, 2007, 1, 45-Eds. J G. de Vries, C. J Elsevier-Wiley-VCH, Weinheim). The use of more stable osmium derivatives, compared to those of ruthenium, has the advantage of allowing to carried out the reduction at higher temperatures.

The invention therefore relates to ligands of the HCNN/CNN type represented by formulas (Ia) and (Ib)

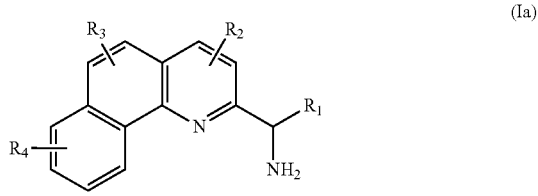

(Ia)

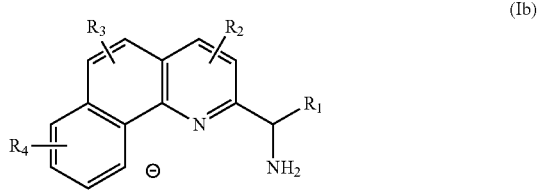

(Ib)

wherein:
$R_1$, is an aliphatic or an aromatic group;
$R_2$, $R_3$ and $R_4$ are equal or different each other and are hydrogen atoms, aliphatic or aromatic groups, halogen atoms, alkoxo groups, nitro groups, cyano groups.

The invention also relates to transition metal complexes represented by the general formula (II)

[MXL$_m$L'] (II)

wherein M, X, L and L' can be:
M a group VIII transition metal selected from iron, ruthenium and osmium;
X a halogen, a hydrogen, an alkoxide (OR where R can be an aliphatic or aromatic group);
L a ligand selected from the groups consisting of:
a) a monodentate phosphine of general formula $PR^1R^2R^3$ where $R^1R^2$ and $R^3$ are equal or different each other and are aliphatic or aromatic groups;
b) a bidentate phosphine of $PR'_2$—Z—$PR''_2$ type where Z is a hydrocarbon chain, optionally substituted, with preference for diphosphines of $PR'_2(CH_2)xPR''_2$ type, with, x being equal to 2, 3 or 4, where R' and R'' are equal or different and are aliphatic or aromatic groups;
c) an optically active diphosphine;
and m is equal to 1 or 2 with the proviso that m is equal to 1 when the ligand L is selected from group b) or c) and is equal to 2 when the ligand L is selected n from group a) and that in this case, the ligands L are equal or different;
L' a tridentate cyclometalated ligand of CNN type of formula (Ib)

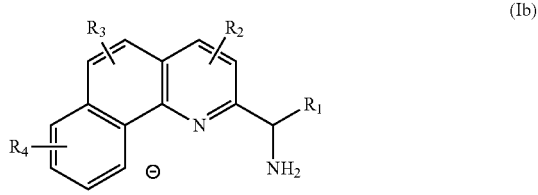

(Ib)

where R1 is H, or an aliphatic or an aromatic group and where $R_2$, $R_3$ and $R_4$ are equal or different each other and are atoms of hydrogen, aliphatic and aromatic groups, halogen atoms, alkoxo groups, nitro groups, cyano groups.

The invention also relates to transition metal complexes represented by the general formula (II)

$$[MXL_mL'] \quad (II)$$

wherein M, X, L, and L' can be:

M a group VIII transition metal selected from iron, ruthenium and osmium;

X a halogen, a hydrogen, an alkoxide (OR where R can be an aliphatic or aromatic group);

L a ligand selected from the groups consisting of:
a) a monodentate phosphine of general formula $PR^1R^2R^3$ where $R^1$, $R^2$ and $R^3$ are equal to or different from each other and are aliphatic or aromatic groups;
b) a bidentate phosphine of $PR'_2$—Z—$PR''_2$ type where Z is a hydrocarbon chain, optionally substituted, with preference for diphosphines of $PR'_2(CH_2)xPR''_2$ type, with x being equal to 2, 3 or 4, where R' and R'' are equal or different and are aliphatic or aromatic groups;
c) an optically active diphosphine;
and M is equal to 1 or 2 with the proviso that M is equal to 1 when the ligand L is selected from group b) or c) and is equal to 2 when the ligand L is selected from group a) and that in this case, the ligands L are equal or different;

L' a tridentate cyclometalated ligand of CNN type of formula (Ib)

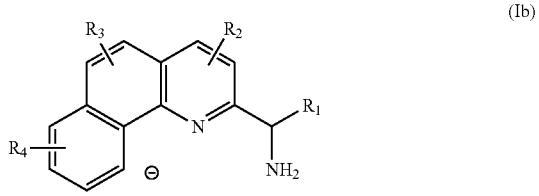

(Ib)

where $R_1$ is H, or an aliphatic or an aromatic group and where $R_2$, $R_3$ and $R_4$ are equal to or different from each other and are atoms of hydrogen, aliphatic or aromatic groups, halogen atoms, alkoxo groups, nitro groups, or cyano groups.

A further aspect of the invention is the process for preparing the transition metal complexes, also obtainable in situ, and the transition metal complexes obtained directly in situ with said processes during the reduction reaction of ketones or aldehydes with molecular hydrogen or by hydrogen transfer from an alcohol to said ketones or aldehydes.

A further aspect of the invention is the use of said transition metal complexes as catalysts for the reduction reaction of carbonyl or imino compounds with hydrogen gas or by hydrogen transfer.

These and other aspects as well as the characteristics and advantages of the present invention will be more apparent from the detailed description below and by the preferred embodiments given as non-limiting illustrations of the invention itself.

BRIEF DESCRIPTION OF THE DRAWINGS

FIG. 1 shows structures of several chiral phosphines useful in the invention.

DETAILED DESCRIPTION OF THE INVENTION

For the purposes of the invention the inventors have identified, in benzo[h]quinoline derivatives with a —$CHR_1$—$NH_2$ group in position 2 represented by the general formula (Ia) and where the benzyl carbon can possibly be a chiral centre, ligands suitable for the synthesis of transition metal complexes to be used as catalysts in reduction reactions of carbonyl compounds by hydrogen transfer or hydrogen gas. Due to their electronic and steno characteristics these ligands are potentially tridentate, being able to coordinate to a metal through the quinolinic nitrogen (sp2) and the primary amine nitrogen (sp3), and also lead to the formation of a metal-carbon a bond and two 5-membered rings by cyclometalation reactions. As a result of research it has been discovered that complexes of various transition metals can be effectively obtained in which ligands derived from benzo[h]quinoline, in the presence of ancillary phosphine-type ligands, function as cyclometalated tridentates forming stable complexes and have interesting applications as catalysts, in the presence of bases, in reduction reactions of carbonyl or imino compounds.

As previously stated the ligands of the invention are a family of benzo[h]quinolone derivatives (HCNN) with a —$CHR_1$,—$NH_2$ group in position 2

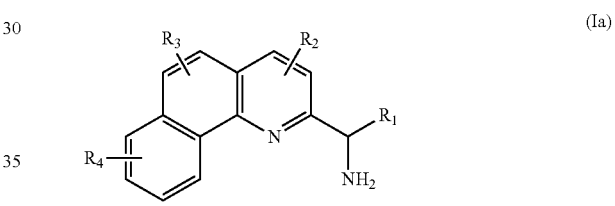

HCNN

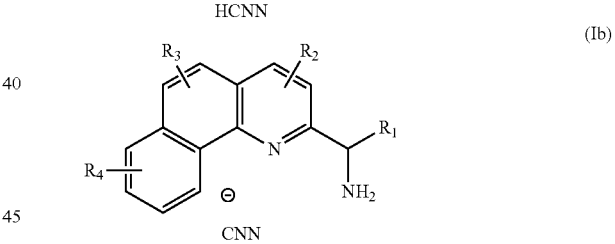

CNN represented by the general formula (Ia) where the benzyl carbon can possibly be a chiral centre, and where $R_1$, can be H, or aliphatic or aromatic groups and where $R_2$, $R_3$ and $R_4$ can be equal or different and be hydrogen atoms, aliphatic and aromatic groups, halogen atoms, alkoxo groups, nitro groups, cyano groups.

In particular the invention relates to a new class of transition metal complexes, of group VIII transition metals selected from iron, ruthenium and osmium, containing the CNN type ligand and phosphines and their use, in the presence of strong bases, as efficient catalysts in catalytic reduction reactions of ketones and aldehydes to alcohols, either by hydrogen transfer or hydrogen gas. When the ligand of benzo[h]quinoline type and/or the phosphines used are optically active, various types of optically active alcohols can be produced starting from carbonyl compounds such as prochiral ketones.

In the presence of mono or bidentate phosphines and a base, such as triethylamine, the HCNN ligands (Ia) react with a suitable precursor of a transition metal selected from iron, ruthenium and osmium, preferably ruthenium and osmium, to give complexes in which they function as tridentate cyclometalated CNN (Ib) ligands coordinating to the metal through the quinolinic nitrogen ($sp^2$) and the primary amine nitrogen ($sp^3$) with formation in position 14 of a metal-carbon σ bond and two 5-membered rings with the following structural formula

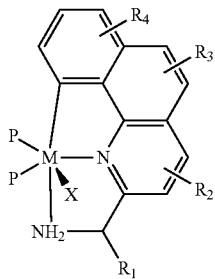

with P=phosphorus atoms of a monodentate or bidentate phosphine.

The various types of ligands of the benzo[h]quinoline family (Ia; HCNN) can be prepared either (R1═H) by reduction of the corresponding 2-cyano derivatives or (R1 aliphatic or aromatic group) by reductions of the suitable 2-ketoxime.

In the presence of mono or bidentate phosphines and a base, such as triethylamine, the HCNN ligands (Ia) react with a suitable precursor of a transition metal selected from iron, ruthenium and osmium, preferably ruthenium and osmium, to give complexes in which they function as tridentate cyclometalated CNN (Ib) ligands coordinating to the metal through the quinolinic nitrogen ($sp^2$) and the primary amine nitrogen ($sp^3$), with formation in position 14 of a metal-carbon σ bond and two 5-membered rings with the following structural formula

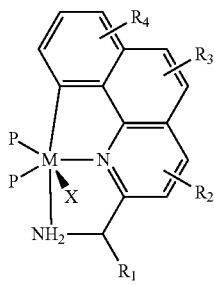

with P=phosphorus atoms of a monodentate or bidentate phosphine.

The syntheses of three different HCNN type ligands (Ia) are given below by way of non-limiting illustration,

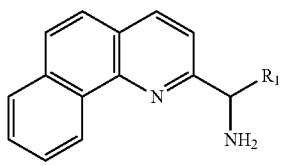

wherein:
R$_1$═R$_2$═R$_3$═R$_4$═H (1) HCNN—H
R$_1$═Me, R$_2$═R$_3$═R$_4$═H (2) HCNN-Me
R$_1$═C(Me)$_3$, R$_2$═R$_3$═R$_4$═H (3)HCNN-$^t$Bu The coordinating properties of those three ligands are very similar to each other and all easily give cyclometalation reactions with Ru(II) and Os(II), and behave as monoanionic tridentate ligands

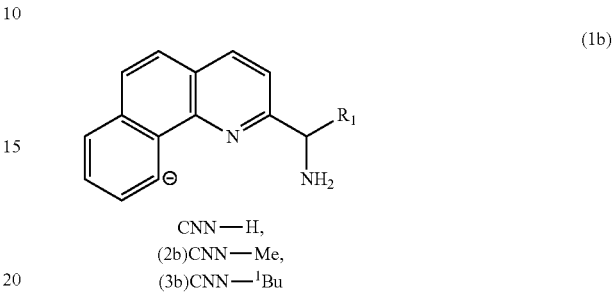

For the preparation of the complexes, those metal precursors containing monodentate phosphines of formula MX$_2$P$_n$ (M═Ru, Os; X═Cl, Br; P═PPh$_3$; n═3,4) are preferably used.

Generally the preparation process of the complexes consists of the reaction, under an inert atmosphere, between the metal precursor, the phosphine ligands and the HCNN ligand in a suitable solvent, being preferably toluene, in the presence of triethylamine, which facilitates cyclometalation.

The complexes of the invention can therefore be of ruthenium(II) and osmium(II) and have the general formula (III) and (IV)

[RuX$_m$L']     (III)

and

[OsXL$_m$L']     (IV)

wherein:
X, L, L' can have the previously stated meanings.

The CNN type ligands of the invention are new and, combined with monodentate or bidentate phosphines, afford group VIII transition metals, preferably ruthenium(II) and osmium(II), complexes, which are particularly active catalysts in the reduction of carbonyl compounds such as ketones with hydrogen gas in alcohols or by hydrogen transfer using 2-propanol as the hydrogen donor.

For the purposes of the present invention, from the combination of the different meanings of X, L, L' and m, and when the transition metal is ruthenium, ruthenium(II) complexes of general formulas given below are obtained:

ruthenium(II) complexes of formula (V)

[RuXL$_2$L']     (V)

wherein:
X is a halogen, a hydrogen, an alkoxide (OR)
L are monodentate phosphines, equal or different, selected from group a);
L' is a tridentate ligand of CNN type of formula (Ib);
ruthenium(II) complexes represented by the formula (VI)

[RuXL$_1$L']     (VI)

wherein:
X is a halogen, a hydrogen, an alkoxide (OR);
L is a bidentate phosphine selected from group b) or an optically active diphosphine selected from group c);
L' is a tridentate ligand of CNN type of formula (Ib).

For the purposes of the present invention the preferred ligand X is chloride or bromide, the preferred ligands L of group a) are $PPh_3$; of group b) are $PPh_2(CH_2)_4PPh_2$; of group c) are:
  (R,S)-JOSIPHOS (12),
  (S,R)-JOSIPHOS* (13),
  (S,S)-SKEWPHOS (14),
  (S)-MeO-BIPHEP (15)
  (as illustrated in FIG. 1);
while the preferred meaning of $R_1$, $R_2$, $R_3$ and $R_4$ of the L' ligand of formula (Ib) is H(CNN—H).

When the transition metal is osmium and m is equal to 2, osmium(II) complexes according to the general formula (VII):

[OsXL$_2$L']      (VII)

are obtained,
wherein:
X is a halogen, a hydrogen, an alkoxide (OR);
L are monodentate phosphines, equal or different, selected from group a);
L' is a tridentate ligand of CNN type of formula (Ib).

When the transition metal is osmium and m is equal to 1, the complexes can be represented by the formula (VIII)

[OsXL$_1$L']      (VIII)

wherein:
X is a halogen, a hydrogen, an alkoxide (OR);
L is a bidentate phosphine selected from group b or an optically active diphosphine selected from group c);
L' is a tridentate ligand of CNN type of formula (Ib).
  For the purposes of the present invention
  the preferred ligand X is the chloride or bromide;
  the preferred ligand L of group b) is $PPh_2(CH_2)_4PPh_2$;
  the preferred ligands L of group c) are (R,S)-JOSIPHOS, (S,R)-JOSIPHOS*, (S,S)-SKEWPHOS, (S)-MeO-BIPHEP
while the preferred meaning of $R_1$, $R_2$, $R_3$ and $R_4$ of the ligand L' of formula (Ib) is H (CNN—H),
  Specific examples of complexes which have been isolated and used in catalysis are given below by way of non-limiting examples of the present invention.

1. Ruthenium Complexes of General Formula (V)

[RuXL$_2$L']      (V)

where L' is the CNN—H ligand, L is $PPh_3$ and X=Cl (6),

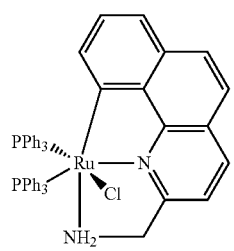

(8)

2. Ruthenium Complexes of General Formula (VI)

[RuXL$_1$L']      (VI)

where L' is the CNN—H ligand, X=Cl or H, and L is the diphosphine $PPh_2(CH_2)_4PPh_2$

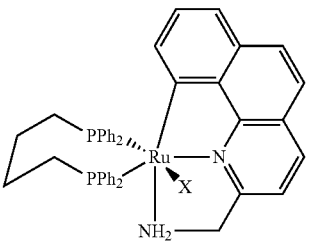

X=Cl (7); X=H (8); X=O—CH(p-$C_6H_4F$)$_2$ (9)
where L'=CNN-Me (10), CNN-Bu$^t$ (11); X=Cl

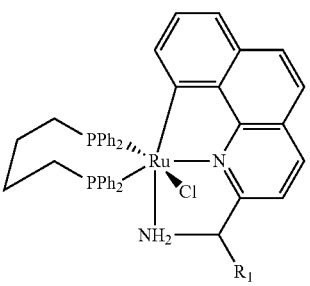

$R_1$=Me (10), Bu$^t$(11)
where L' is the CNN—H ligand and where L is a chiral diphosphine represented as
  (R,S)-JOSIPHOS (12),
  (S,R)-JOSIPHOS* (13),
  (S,S)-SKEWPHOS (14),
  (S)-MeO-BIPHEP (15)
  (as illustrated in FIG. 1).

The synthesis method for the complexes of RuCl[P—P*](CNN—H) type, in which P—P* represents chiral diphosphine, leads to the formation of mixtures of different diastereomers, as shown by the $^{31}$P NMR spectrum of the products isolated. The diastereomeric mixtures obtained have been used as such in the catalytic tests.

3. Osmium(II) Complexes of Formula (VIII)

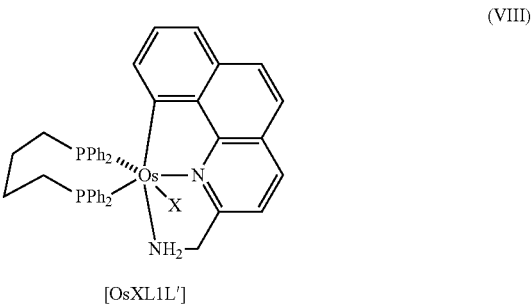

(VIII)

[OsXL1L']

where L' is the CNN—H ligand, L is the diphosphine $PPh_2(CH_2)_4PPh_2$ and X=Cl (7a);
X=H (8a); X=O—CH(p-$C_6H_4F$)$_2$ (9a).

A. Ligand Synthesis

The synthesis path used for the HCNN ligand in the form in which $R_1$=$R_2$=$R_3$=$R_4$=H is schematically represented in scheme 1

Scheme 1

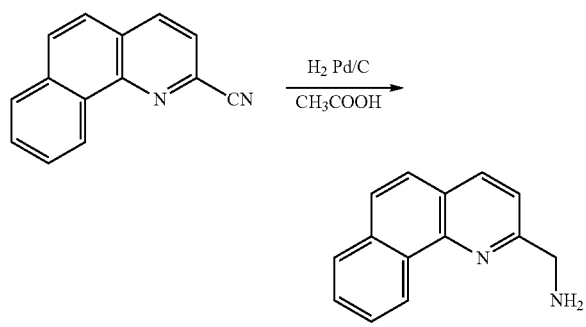

The 2-cyanobenzo[h]quinoline, prepared by the method published by Chelucci et al. (*Tetrahedron: Asymmetry* 1999, 10, 543) was reduced with hydrogen gas in acetic acid in the presence of 10% Pd on carbon.

The ligands with $R_1$=Me, $CMe_3$ in racemic form were prepared by the methods summarized in the following schemes starting from 2-bromobenzo(h)quinoline (scheme 2) which can be obtained from 2-chlorobenzo(h)quinoline prepared by the method of Cappelli et al. (*J. Med. Chem.* 1998, 41, 728).

Scheme 2

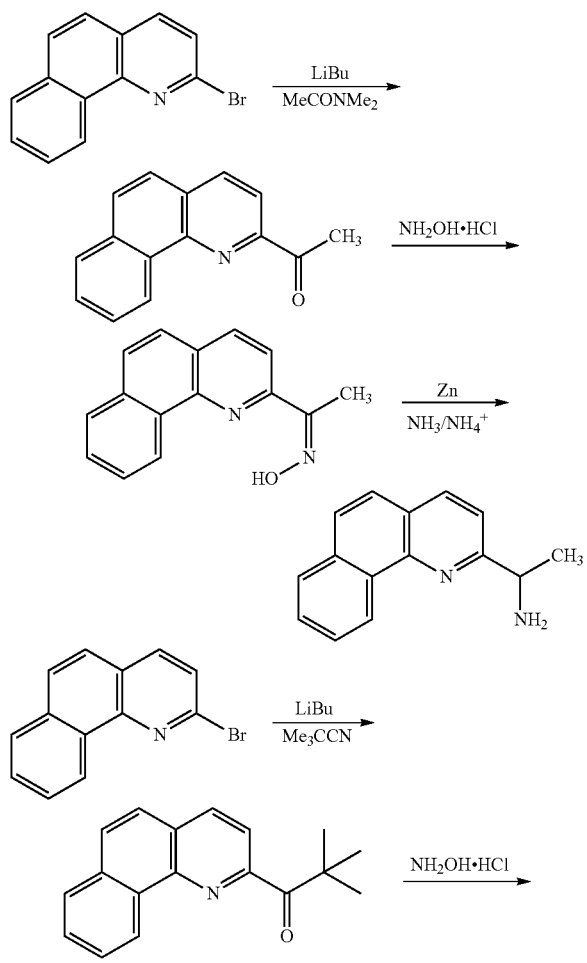

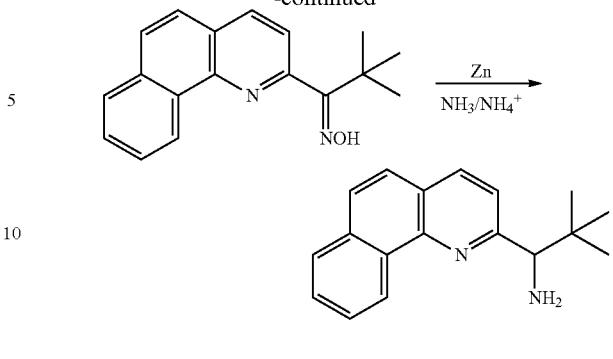

These syntheses are given in examples 1-3.

B. Synthesis of Ruthenium Complexes

The synthesis of the complexes (6-15) of the invention involves the compound $RuCl_2(PPh_3)_3$(4) as starting product

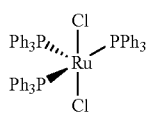 (4)

which is commercially available or can be prepared by reaction between $RuCl_3$ hydrate and triphenylphosphine (R. Holm, *Inorg. Synth.* 1970, 12, 238), while the complex $RuCl_2[PPh_2(CH_2)_4PPh_2](PPh_3)$ (5)

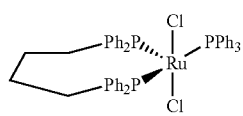 (5)

was prepared according to the procedure published in the literature (C. W. Jung, P. E. Garrou, P. R. Hoffman, K. G. Caulton, *Inorg. Chem.* 1964, 23, 726).

The complex (6) was obtained by reacting $RuCl_2(PPh_3)_3$(4) with HCNN—H (1) in toluene under reflux in the presence of triethylamine. Following the procedure of (6) the derivative (7) was obtained from reacting (5) with HCNN—H (1), while the complexes (10) and (11) were prepared with HCNN-Me (2) and with HCCN-tBu (3). The catalysts (12-15) were prepared by reacting the chiral phosphine with the complex (4) in toluene under reflux followed by addition of the HCNN—H ligand (1) in the presence of triethylamine. The derivatives (8) and (9) were prepared from (7) by reaction with sodium isopropoxide and adding 4,4'-difluorobenzophenone in the case of (9).

All the operations were carried out under inert gas atmosphere, the solvents used being dried and distilled before use. The syntheses are given in examples 4-13.

C. Synthesis of Osmium Complexes

The synthesis of the complex (7a) of the invention involves the compound $OsCl_2(PPh_3)_3$(4a) as the starting product, which can be prepared by reacting $[(NH_4)_2OsCl_6]$ with triphenylphosphine (Elliott, G. P., McAuley, N. M., Roper, W. R., *Inorg. Synth*, 1989, 26, 1849)

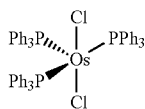

(4a)

while the complex OsCl$_2$(CNN—H)[PPh$_2$(CH$_2$)$_4$PPh$_2$] (7a) was prepared by reacting OsCl$_2$(PPh$_3$)$_3$ with phosphine PPh$_2$(CH$_2$)$_4$PPh$_2$ in methylene chloride and subsequent treatment of the thus obtained product with HCNN—H (1) in toluene under reflux and in the presence of triethylamine.

The derivatives (8a) and (9a) were prepared from (7a) by reaction with sodium isopropoxide and adding 4,4'-difluorobenzophenone in the case of (9a).

The synthesis is given in the examples 14-16.

The syntheses and characterizations of the ruthenium(II) complexes (6-15) and osmium(Ii) complexes (7a-9a) are given in detail hereinafter. All the syntheses were carried out under argon atmosphere, using distilled or previously deaerated solvents.

The ligands and complexes were characterized by elemental analysis and $^1$H NMR, $^{13}$C {$^1$H} NMR and $^{31}$P {$^1$H} NMR nuclear magnetic resonance measurements. All the complexes with the CNN—R ligands exhibited a characteristic signal for the carbon bonded to the metal at 6=177 to 183 ppm when the metal is ruthenium, and at σ=157 ppm when the metal is osmium.

Example 1: Preparation of the HCNN—H Ligand

The compound was obtained from 2-cyanobenzo[h]quinoline prepared by the method given in: Chelucci, G. et al., *Tetrahedron. Asymmetry* 1999, 10, 543.

1-(Benzo[h]quinolin-2-yl)methanamine

A mixture of 2-cyanobenzo[h]quinoline (2.04 g, 10.0 mmol) and 10% palladium on carbon (0.40 g) in acetic acid (120 nil) was hydrogenated at ambient temperature, in a Parr reactor, with hydrogen gas at a pressure of 2 atm. After 4 hours, during which time absorbance of two hydrogen equivalents was observed, the reaction mixture was filtered and the solvent evaporated under reduced pressure. The oily residue was taken up with ethyl ether and the mixture washed with a 10% NaOH solution until an alkaline pH was achieved. The organic phase was then separated and dried over Na$_2$SO$_4$. The solvent was evaporated and the residue was purified by flash chromatography using MeOH as eluent, 1.87 g (90% yield) of 1-(benzo[h]quinolin-2-yl) methanamine in the form of a red solid was obtained.

Elemental analysis (%) calculated for C$_{14}$H$_{12}$N$_2$: C, 80.74; H, 5.81; N, 13.45. Found. C, 80.55; H, 5.91; N, 13.66. $^1$H NMR (CDCl$_3$): δ 9.58 (d, J=7.4 Hz, $^1$H, aromatic proton), 8.11-7.71 (n, 7H; aromatic protons), 4.37 (s, 2H; CH$_2$), 2.90 (s, 211; NH$_2$), $^{13}$C{$^1$H} NMR (CDCl$_3$): δ 158.5 (s, NCCH$_2$; aromatic carbon), 143.9 (s, NCC; aromatic carbon), 134.4-118.2 (m; aromatic carbons), 46.3 (s; CH$_2$).

The starting product for the synthesis of the two HCNN—R ligands (R=Me, $^t$Bu) (examples 1 and 2) was the 2-bromobenzo[h]quinoline obtained from 2-chlorobenzo[h] quinoline prepared by the method given by Cappelli, A. et al., *J. Med. Chem.* 1998, 41, 728.

Example 2: Preparation of the HCNN-Me Ligand

The ligand was obtained by reduction with Zn of (benzo [h]quinolin-2-yl)methyllcetoxime, prepared by reacting 1-(benzo[h]quinolin-2-yl)ethanone with NH$_2$OH.HCl.

2-Bromobenzo[h]quinoline

A mixture of 2-chlorobenzo[h]quinoline (2.43 g, 11.4 mmol), bromotrimethylsilane (3.00 ml, 22.7 mmol) and propionittile (12 ml) was heated under reflux for 111 hours. The reaction mixture was then poured into a 10% NaOH solution containing ice. The organic phase was separated and the aqueous phase extracted with Et$_2$O (3×15 ml). The organic phases were combined, dried over anhydrous Na$_2$SO$_4$ and the solvent evaporated under reduced pressure. The residue was purified by chromatography (SiO$_2$, petroleum ether/acetate=9/1) to give 2-bromobenzo[h]quinoline in the form of a yellow solid: 2.82 g (96% yield); melting point: 113-114° C.

Elemental analysis (%) calculated for C$_{13}$H$_8$BrN: C, 60.49; H, 3.12; N, 5.43, Found. C, 60.33; H, 3.25; N, 5.38. $^1$H NMR (CDCl$_3$): 9.35-9.15 (m, 1H), 7.96 (d, J=8.4 Hz, 1H), 7.92-7.84 (m, 1H), 7.81 (d, J=8.4 Hz, 1H), 7.74-7.67 (m, 2H), 7.61 (dd, J=8.4 Hz, J=1.5 Hz, 2H). $^{13}$C{$^1$H}NMR (CDCl$_3$): δ 147.1, 140.7, 138.0, 133.7, 130.4, 128.7, 128.2, 127.7, 127.3, 126.1, 125.1, 124.7, 124.5.

1-(Benzo[h]quinolin-2-yl)ethanone

A solution of 2-bromobenzo[h]quinoline (1.52 g, 5.89 mmol) in THF (36 ml) was cooled to −78° C. After 10 minutes a solution of 2.5 M n-butyllithium in n-hexane (2.47 ml, 6.18 mmol) was added. The resulting dark red solution was again stirred at −78° C. for 1 hour after which N,N-dimethylacetamide (0.60 mi, 6.45 mmol) was added dropwise. The solution was stirred for 1 h at −78° C. and allowed to warm slowly to ambient temperature. A solution of 1 M HCl (7.4 ml, 7.4 mmol) was then added to the organic phase was separated and the aqueous phase was extracted with Et$_2$O (2×15 ml). The organic phases were combined, dried over anhydrous Na$_2$SO$_4$ and the solvent evaporated under reduced pressure. The residue was purified by flash chromatography (petroleum ether/acetate=95/5) to give 1.00 g (77% yield) of 1-(benzo[h]quinolin-2-yl)ethanone in the form of a yellow solid: mp 113-115° C.

Elemental analysis (%) calculated for C$_{15}$H$_{11}$NO: C, 81.43; H, 5.01; N, 6.33. Found: C, 81.43; H, 5.01; N, 6.33. $^1$H NMR (CDCl$_3$): δ 9.08 (dd, J=8.1 Hz, J=1.5 Hz, 1H), 8.02 (d, J=8.1 Hz, 1H), 7.92 (d, J=8.1 Hz, 1H), 7.80-7.70 (m, 1H), 7.69-7.55 (rn, 3H), 7.39 (d, J=9 Hz, 1H), 2.83 (s, 3H), $^{13}$C{$^1$H} NMR (CDCl$_3$): δ 200.2, 151.0, 144.8, 135.9, 133.3, 131.1, 129.5, 128.2, 127.8, 127.6, 127.1, 124.5, 124.1, 118.3, 25.4.

Oxime of 1-(benzo[h]quinolin-2-yl)ethanone

A solution of 1-benzo[h]quinolin-2-yl)ethanone (2.62 g, 11.84 mmol) and hydroxylamine hydrochloride (1.52 g, 21.87 mmol) in 96% ethanol (100 ml) was stirred at ambient temperature for 30 hours, The reaction was monitored by TLC (SiO$_2$, petroleum ether/acetate=9/1), Most of the solvent was then evaporated under reduced pressure and the residue taken up with CH$_2$Cl$_2$ and a saturated NaHCO$_3$ solution. The resulting mixture was vigorously stirred for 30 minutes, then the organic phase was separated and the aqueous phase was extracted with CH$_2$Cl$_2$ (2×20 ml). The organic phases were combined, dried over anhydrous Na$_2$SO$_4$ and the solvent evaporated to give 2.70 g (97% yield) of the oxime of 1-(benzo[h]quinolin-2-yl)ethanone in the form of a yellow solid which was used in the next stage without further purification: melting point 200-202° C.

Elemental analysis (%) calculated for C$_{15}$H$_{12}$N$_2$O: C, 76.25; H, 5.12; N, 11.86. Found: C, 76.44; H, 5.15; N, 11.89.

1-(Benzo[h]quinolin-2-yl)ethanamine

A solution of the oxime of 1-(benzo[h]quinolin-2yl)ethanone (2.60 g, 11.0 mmol) and ammonium acetate (1.05 g, 13.6 mmol) in a mixture consisting of 30% NH$_3$/H$_2$O/96% EtOH (39.5/26.3/26.3 ml) was stirred at ambient temperature for 30 minutes. Zinc in powder form (3.95 g, 60.4 mmol) was then added in small portions (at ambient temperature) over a period of 2 hours, and the resulting mixture was heated under reflux for 3 hours. The grey precipitate formed was filtered off under reduced pressure and the solvent was evaporated to give a residue that was alkalized with 10% NaOH, and extracted with Et$_2$O (3×30 ml). The organic phases were combined, dried over anhydrous Na$_2$SO$_4$ and the solvent evaporated under reduced pressure. The residue was purified by flash chromatography using MeOH as eluent to give 1.88 g (77% yield) of 1-(benzo[h]quinolin-2-yl)ethanamine in the form of an orange coloured oil.

Elemental analysis (%) calculated for C$_{15}$H$_{14}$N$_2$: C, 81.05; H, 8.35; N, 12.60. Found: C, 81.24; H, 6.38; N, 12.58. $^1$H NMR (CDCl$_3$): δ 9.36 (d, J=8.1 Hz, 1H), 8.08 (d, J=8.1 Hz, 1H), 7.88 (d, J=8.1 Hz, 1H), 7.80-7.59 (m, 4H), 7.47 (d, J=8.1 Hz, 1H), 4.37 (q, J=66 Hz, 1H), 2.26 (s, 2H), 1.56 (d, J=6.6 Hz, 3H). $^{13}$C {$^1$H} NMR (CDCl$_3$): δ 164.2, 145.5, 136.3, 133.6, 131.3, 127.9, 127.7, 127.0, 126.7, 125.1, 124.9, 124.3, 119.0, 52.8, 24.8.

Example 3: Preparation of the HCNN-Bu$^t$ Ligand

The ligand was obtained by reduction with Zn of (benzo[h]quinolin-2-yl)-t-butyl ketoxime prepared by reacting NH$_2$OH.HCl with 1-(benzo[h]quinolin-2-yl)-2,2-dimethylpropanone.

1-Benzo[h]quinolin-2-yl)-2,2-dimethylpropanone

A solution of 2-bromobenzo[h]quinoline (1.52 g, 5.89 mmol) in THF (36 ml) was cooled to −78° C. and after 10 minutes a solution of 2.5 M of n-butyllithium in n-hexane (2.47 ml, 6.18 mmol) was added slowly. The resulting dark red solution was stirred at this temperature for 1 hour and then a solution of 2,2-dimethylpropanonitrile (0.78 ml, 7.04 mmol) in THF (5 mi) was added drop-wise. The solution was stirred for a further hour at −78° C. and finally allowed to warm slowly to ambient temperature. A solution of 1M H$_2$SO$_4$ (25 ml, 25 mmol) was then added and the mixture was heated under reflux for 3 hours. After cooling, the organic phase was separated and the aqueous phase was extracted with Et$_2$O (3×15 ml). The organic phases were combined, dried over anhydrous Na$_2$SO$_4$ and the solvent evaporated under reduced pressure. The residue was purified by flash chromatography (eluent: petroleum ether/acetate=9/1) to give 1.24 g (80% yield) of 1-(benzo[h]quinolin-2-yl)-2,2-dimethylpropanone in the form of a yellow solid; melting point: 88-90° C.

Elemental analysis (%) calculated for C$_{18}$H$_{17}$NO: C, 82.10; H, 6.51; N, 5.32. Found. C, 82.10; H, 6.51, N, 5.32. $^1$H NMR (CDCl$_3$): δ 9.20 (d, J=7.8 Hz 1H), 8.13 (s, 2H), 7.84 (d, J=7.8 Hz, 1H), 7.80-7.73 (m, 2H), 7.73-7.62 (m, 1H), 7.56 (d, J=9 Hz, 1H), 1.67 (s, 9H). $^{13}$C{$^1$H} NMR (CDCl$_3$); δ 206.7, 152.1, 144.5, 136.3, 133.7, 131.8, 129.5, 128.4, 127.9, 127.5, 124.9, 124.5, 121.2, 44.3, 28.0.

Oxime of 1-(benzo[h]quinolin-2-yl)-2,2-dimethylpropanone

A solution of 1-(benzo[h]quinolin-2-yl)-2,2-dimethylpropanone (1.30 g, 4.94 mmol) and hydroxylamine hydrochloride (0.63 g, 9.07 mmol) in 96% ethanol (45 nil) was stirred at ambient temperature for 36 hours, The reaction was monitored by TLC (SiO$_2$; eluent: petroleum ether/acetate=9/1). The solvent was evaporated under reduced pressure and the residue taken up with CH$_2$Cl$_2$ and a saturated NaHCO$_3$ solution. The resulting mixture was vigorously stirred for 30 minutes, then the organic phase was separated. The aqueous phase was extracted with CH$_2$Cl$_2$ (2×20 ml). The organic phases were combined, dried over anhydrous Na$_2$SO$_4$ and the solvent evaporated to give 0.69 g (50% yield) of the oxime of 1-(benzo[h]quinolin-2-yl)-2,2-dimethylpropanone in the form of a light brown solid which was used in the next stage without further purification: melting point 234-236° C.

Elemental analysis (%) calculated for C$_{18}$H$_{18}$N$_2$O: C, 77.67; H, 6.52; N, 10.06. Found: C, 77.55; H, 6.55; N, 10.02.

1-(Benzo[h]quinolin-2-yl)-2,2-dimethylpropanamine

A solution of the oxime of 1-(benzo[h]quinolin-2-yl)-2,2-dimethylpropanone (1.30 g, 4.67 mmol) and ammonium acetate (0.447 g, 5.80 mmol) in a mixture consisting of 30% NH$_3$/H$_2$O/96% EtOH was stirred at ambient temperature for 30 minutes. Zinc in powder form (1.68 g, 25.7 mmol) was added in small portions (at room temperature) over a period of 2 hours, and the resulting mixture was heated under reflux for 4 hours. After cooling, the mixture was treated with an aqueous solution of 36% HCl up to pH=1 and concentrated under reduced pressure. The residue was treated with an aqueous solution of 50% KOH, and the solution was extracted with Et$_2$O (4×25 ml). The organic phases were combined, dried over anhydrous Na$_2$SO$_4$ and the solvent evaporated under reduced pressure. The residue was purified by flash chromatography using MeOH as eluent to give 1-(benzo[h]quinolin-2-yl)-2,2-dimethylpropanamine in the form of an orange oil: 0.59 g (48% yield).

Elemental analysis (%) calculated for C$_{15}$H$_{20}$N$_2$: C, 81.78; H, 7.63; N, 10.60. Found. C, 81.66; H, 7.67; N, 10.63. $^1$H NMR (CDCl$_3$): δ 9.31 (d, J=8.1 Hz, 1H), 7.98 (d, J=8.1 Hz, 1H), 7.84 (d, J=7.5 Hz 1H), 7.76-1.55 (m, 4H), 7.34 (d, J=8.1 Hi, 1H), 3.88 (s, 1H), 2.65 (s, 2H), 0.99 (s, 9H). $^{13}$C{$^1$H} NMR (CDCl$_3$): δ 161.1, 145.1, 134.8, 133.4, 131.4, 127.8, 127.5, 126.8, 126.6, 125.0, 124.8, 124.3, 122.2, 65.8, 35.5, 26.5.

Example 4: Synthesis of the Complex [RuCl(PPh$_3$)$_2$(CNN—H)] (6)

The complex RuCl$_2$(PPh$_3$)$_3$ (4) (0.150 g, 0.156 mmol) suspended in 2 ml of distilled toluene, was reacted with HCNN—H (1) (36 mg, 0.174 mmol) and triethylamine (0.22 ml, 0.158 mmol). After stirring the mixture for 2 hours at 110° C. the solution volume was reduced to about half and the complex was precipitated by adding 2 ml of pentane. The solid obtained was filtered off, washed with pentane (3×5 ml) and dried under reduced pressure. Yield: 100 mg (74%).

Elemental analysis (%) calculated for C$_{50}$H$_{41}$ClN$_2$P$_2$Ru: C, 69.16; H, 4.76; N, 3.23. Found: C, 69.35; H, 4.85; N, 3.34. $^{31}P\{^1H\}$ NMR (81.0 MHz, $CD_2Cl_2$, 20° C., $H_3PO_4$): δ 56.5 (d, J(PP)=33.4 Hz), 50.5 (d, J(PP) 33.4 Hz).

Example 5: Synthesis of the Complex $RuCl[PPh_2(CH_2)_4PPh_2](CNN—H)$ (7)

The complex $RuCl_2(PPh_3)[PPh_2(CH_2)_4PPh_2]$ (5) (800 mg, 0.929 mmol) was added to a solution of the HCNN—H (1) ligand (232 mg, 1.11 mmol) and triethylamine (1.55 ml, 11.1 mmol) in 2-propanol (15 ml). The mixture was refluxed for 2 hours and the orange precipitate obtained was filtered off; washed with methanol (3×10 ml) and dried under reduced pressure. Yield: 608 mg (85%).
Elemental analysis (%) calculated for $C_{42}H_{39}ClN_2P_2Ru$: C, 65.49: H, 5.10; N, 3.64. Found: C, 65.18; H, 5.23; N, 3.47. $^1H$ NMR (200.1 MHz $CD_2C_2$, 20° C., TMS): δ 8.19 (pseudo t, J(HH)=7.6 Hz, 2H; aromatic protons), 7.99 (d, J(HH)=7.0 Hz, 1H; aromatic proton), 7.82 (pseudo t, J(HH)=8.0 Hz, 2H; aromatic protons), 7.64 (d, J(H11)=8.5 Hz, 2H; aromatic protons), 7.52-7.20 (m, 14H; aromatic protons), 6.98 (d, J(HH)=8.2 Hz, 1H; aromatic proton), 6.45 (t, J(HH)=7.3 Hz, 1H; aromatic proton), 6.16 (pseudo t, J(HH)=7.8 Hz, 2H; aromatic protons), 5.47 (t, J(HH)=8.1 Hz, 2H; aromatic protons), 4.37 (dd, J(HH)=16.3, 5.4 Hz, 1H, $CH_2N$), 3.96 (ddd, J(HH)=16.4, 11.0, 5.0 Hz, 1H; $CH_2N$), 3.60 (In, IH; $NH_2$), 3.01 (m, 2H; $CH_2$), 2.35-1.00 (m, 7H; $CH_2+NH_2$). $^{13}C\{^1H\}$ NMR (50.3 MHz, $CDCl_3$, 20° C., TMS): δ 177.0 (dd, J(CP)=16.6, 8.3 Hz; CRu), 154.3 (s; NCC), 152.3 (d, J(CP)=1.0 Hz; $NCCH_2$), 146.2-115.5 (m; aromatic carbons), 52.2 (d, J(CP)=2.8 Hz; $CH_2N$), 33.1 (dd, J(CP)=24.8, 1.8 Hz; $CH_2$), 29.9 (d, J(CP)=31.9 Hz; $CH_2$), 26.5 (d, J(CP)=1.3 Hz; $CH_2$), 21.5 (dd, J(CP)=2.5, 2.0 Hz; $CH_2$). $^{31}P\{^1H\}$NMR (81.0 MHz, $CD_2Cl_2$, 20° C., $H_3PO_4$); δ 57.3 (d, J(PP)=38.2 Hz), 43.7 (d, J(PP)=38.2 Hz).

Example 6: Synthesis of the Complex $RuH[PPh_2(CH_2)_4PPh_2](CNN—H)$ (8)

The complex $RuCl[PPh_2(CH_2)_4PPh_2(CNN—H)]$ (7) (150 mg, 0.195 mmol) was suspended in toluene (2.9 ml) and a solution of 0.1 M $NaO^iPr$ (2.9 ml, 0.202 mmol) in 2-propanol was added. The mixture was stirred at 60° C. for 1 h. The resulting dark red solution was concentrated to half volume, stirred at RT for 1 h and after addition of toluene (3 ml), kept at −20° C. for 18 h to afford the precipitation of NaCl, which was filtered on celite (fine frit). The solution was stirred under $H_2$ (1 atm) at RT for 1 h, and the solvent was eliminated obtaining a bright orange product, which was dried under reduced pressure. Yield; 119 mg (83%).
Elemental analysis (%) calculated for $C_{42}H_{40}N_2P_2Ru$: C, 68.56; H, 5.48; N, 3.81. Found: C, 68.20, 11, 5.44; N, 3.45. $^1H$ NMR (200.1 MHz, $C_6D_6$, 20° C., TMS). δ 8.58 (t, J(HH)=8.2 Hz, 2H; aromatic protons), 8.40-6.80 (m, 18H; aromatic protons), 6.37 (d, J(HH)=6.8 Hz, 1H; aromatic proton), 6.27 (d, J(HH)=7.7 Hz, 2H; aromatic protons), 6.14 (n, 2H, aromatic protons), 5.50 (t, J(HH)=6.5 Hz, 2H; aromatic protons), 3.20-1.45 (m, 12H; $CH_2$, $NH_2$), −5.40 (dd, J(HP)=90.0, 26.2 Hz, 1H; Ru—H). $^{31}P\{^1H\}$ NMR (81.0 MHz, $C_6D_6$; 20° C. $H_3PO_4$): δ 66.6 (d, J(PP)=16.7 Hz), 35.0 (d, J(PP)=16.7 Hz). IR (Nujol) v=1741.6 $cm^{-1}$ (br. Ru—H).

Example 7: Synthesis of the Complex $Ru[O—CH(p-C_6H_4F)_2][PPh_2(CH_2)_4(PPh_2](CNN—H)$ (9)

The complex $RuCl[PPh_2(CH_2)_4PPh_2(CNN—H)]$ (7) (200 mg, 0.260 mmol) was suspended in toluene (3.9 ml) and a solution of 0.1 M $NaO^iPr$ (3.9 ml, 0.390 mmol) in 2-propanol was added. The suspension was stirred at 60° C. for 2 hours. The dark red mixture obtained was stirred at ambient temperature for 1 hour, then cooled to −20° C. for 24 hours, to promote precipitation of NaCl which was removed by filtration through celite (fine frit). 4,4'-difluorobenzophenone (68.0 mg, 0.312 mmol) was added to the solution, which was then stirred for 30 minutes at ambient temperature. The solvent was removed by evaporation at reduced pressure and the residue was treated with toluene (2 ml). The mixture was kept at −20° C. for 2 hours, filtered through celite (fine frit) and the filtrate was concentrated to about 1 ml. Addition of pentane led to the precipitation of an orange-red product which was recovered by filtration and dried under reduced pressure. Yield: 186 mg (75%).
Elemental analysis (%) calculated for $C_{55}H_{48}F_2N_2OP_2Ru$: C, 69.24; H, 5.07; N, 2.94. Found. C, 69.16; H, 5.29; N, 2.93. $^1H$ NMR (200.1 MHz, $C_6D_6$, 20° C., TMS). δ 8.15 (m, 2H; aromatic protons), 8.03 (t, J(HH)=7.60 Hz, 2H; aromatic protons), 7.66-6.25 (m, 2611; aromatic protons), 6.02 (t, J(HH)=7.8 Hz, 2H; aromatic protons), 5.86 (d, J(HH)=8.0 Hz, 1H; aromatic proton), 5.41 (t, J(HH)=8.2 Hz, 2H; aromatic protons), 5.28 (broad s, 1H; $NH_2$), 4.46 (d, J(HP)=3.3 Hz, 1H; OCH), 3.24-2.65 (m, 4H; $CH_2$, $NH_2$), 2.35-0.80 (n, 7H, $CH_2$, $NH_2$). $^{13}C\{^1H\}$NMR (50.3 MHz, $C_6D_6$, 20° C. TMS): 183.4 (dd, J(CP) 15.0, 8.5 Hz, CRu), 161.1 (d, J(CF)=240.6 Hz; C—F), 160.6 (d, J(CF)=240.2 Hz; (C—F), 156.0-113.4 (m; aromatic carbons), 79.9 (s, OCH), 52.0 (d, J(CP)=2.5 Hz; $CH_2N$), 31.3 (d, J(CP)=28.3 Hz; $CH_2P$), 30.7 (d, J(CP)=29.5 Hz; $CH_2P$), 26.8 (s, $CH_2$), 22.3 (d, J(CP)=2.3 Hz; $CH_2$). $^{31}P\{^1H\}$ NMR (81.0 MHz, $C_6D_6$, 20° C., $H_3PO_4$): δ 57.0 (d, J(PP)=34.3 Hz), 40.3, (d, J(PP)=34.3 Hz). $^{19}F\{^1H\}$ NMR (188.3 MHz; $C_6D_6$, 20° C.). δ−119.6, −120.3.

Example 8: Synthesis of the Complex $RuCl[PPh_2(CH_2)_4PPh_2](CNN-Me)$ (10)

The complex $RuCl_2[PPh_2(CH_2)_4PPh_2](PPh_3)$ (5) (0.100 g, 0.116 mmol), HCNN-Me (2) (39 mg, 0.175 mmol) and triethylamine (0.16 ml, 1.15 mmol) in 2 ml of 2-propanol were heated under reflux for 3 hours. The precipitate obtained by addition of pentane was filtered off, and washed with pentane (4×3 ml). The solid was suspended in dichloromethane (0.5 ml) and kept at −20° C. overnight. After filtration, the volume of the solution was reduced to one half and pentane (2 ml) was added. The precipitate obtained was filtered off, washed with 2 ml of pentane and dried under reduced pressure. Yield: 60 mg (66%).
Elemental analysis (%) calculated for $C_{43}H_{41}ClN_2P_2Ru$: C, 65.85; H, 5.27; N, 3.57. Found C, 66.10; H, 5.40; N, 3.74. $^1H$ NMR (200.1 MHz, $CD_2Cl_2$, 20° C., TMS): δ 8.18 (pseudo t, J(HH)=8.0 Hz, 2H, aromatic protons), 8.01 (d, J(HH)=7.0 Hz, 1H; aromatic proton), 7.82 (pseudo t, J(HH)=8.4 Hz, 2H; aromatic protons), 7.68 (d, J(HH)=5.4 Hz, 1H; aromatic proton), 7.65 (d, J(HH)=6.0 Hz, 1H; aromatic proton), 7.49-7.22 (m, 14H; aromatic protons), 6.98 (d, J(HH)=8.4 Hz, 1H; aromatic proton), 6.45 (t, J(HH)=7.4 Hz, 1H; aromatic proton), 6.16 (pseudo t, J(HH) 8.2 Hz, 2H; aromatic protons), 5.45 (t, J(HH)=8.4 Hz, 2H; aromatic protons), 4.37 (m, 1H; CHMeN), 3.55 (t, J(HH)=11.4 Hz, 1H; $NH_2$), 3.20-2.85 (m, 3H; $CH_2$), 2.40-1.70 (m, 6H; $CH_2+NH_2$), 1.58 (d, J(HH)=6.7 Hz, 3H; CMe). $^{13}C(^1H)$ NMR (50.3 MHz, $CD_2Cl_2$, 20° C.): δ 179.1 (dd, J(CP)=16.3, 8.4 Hz; CRu), 157.8-116.5 (m; aromatic carbons), 58.5 (d, J(CP)=2.6 Hz; CHN), 33.3 (dd, J(CP)=24.9, 2.2 Hz; $CH_2P$), 30.5 (d, J(CP)=32.1 Hz; $CH_2P$), 26.8 (d, J(CP)=2.0 Hz; CH$_2$), 23.4 (s; Me), 22.0 (m, Hz; CH$_2$), $^{31}$P {$^1$H} NMR (81.0 MHz, CD$_2$Cl$_2$, 20° C., H$_3$PO$_4$): δ 57.3 (d, J(PP)=38.3 Hz), 43.6 (d, J(PP)=38.3 Hz).

Example 9: Synthesis of the Complex RuCl[PPh$_2$(CH$_2$)$_4$PPh$_2$](CNN-$^t$Bu) (11)

The complex RuCl$_2$[PPh$_2$(CH$_2$)$_4$PPh$_2$](PPh$_3$) (5) (0.100 g, 0.116 mmol), HCNN-$^t$Bu (3) (46 mg, 0.174 mmol) and triethylamine (0.16 ml, 1.15 mmol) were added to 2 ml of 2-propanol and refluxed for 5 hours. The solution was then concentrated and the precipitate obtained by addition of pentane was filtered off, washed with pentane (4×3 ml) and dried under reduced pressure. The solid was suspended in dichloromethane (0.5 ml) and kept overnight at –20° C. After filtration, the volume of the solution was reduced to one half and pentane (2 ml) was added. The precipitate was filtered off, washed with 2 ml of pentane and dried under reduced pressure. Yield: 50 mg (52%).

Elemental analysis (%) calculated for C$_{46}$H$_{47}$ClN$_2$P$_2$Ru: C, 66.86; H, 5.73; N, 3.39. Found C, 67.10; H, 5.70; N, 3.19. $^1$H NMR (200.1 MHz, CD$_2$Cl$_2$, 20° C., TMS): δ 8.08 (pseudo t, J(HH)=9.5 Hz, 2H; aromatic protons), 7.98 (d, J(HH)=6.9 Hz, 1H; aromatic proton), 7.71 (pseudo t, J(HH)=8.4 Hz, 2H, aromatic protons), 7.53 (d, J(HH)=8.7 Hz, 1H; aromatic proton), 7.51 (d, J(HH)=8.5 Hz, 1H, aromatic proton), 7.39-7.19 (m, 14H; aromatic protons), 7.11 (d, J(HH)=8.8 Hz, 1H; aromatic proton), 6.33 (pseudo t, J(HH)=8.0 Hz, 1H; aromatic proton), 6.03 (pseudo t, J(HH)=8.0 Hz, 2H, aromatic protons), 5.32 (t, 0.1(HH)=8.4 Hz, 2H; aromatic protons), 3.60-3.36 (m, 2H; CH$^t$BuN+NH$_2$), 3.09-2.84 (m, 3H; CH$_2$), 2.24-1.40 (m, 6H; CH$_2$+NH$_2$), 0.91 (s, 9H $^t$Bu). $^{13}$C($^1$H) NMR (50.3 MHz, CD$_2$Cl$_2$, 20° C.): δ 180.3 (dd, J(CP)=16.7, 8.1 Hz; CRu), 155.5-118.8 (m; aromatic carbons), 72.9 (s; d, J(CP)=2.9 Hz; CHN), 35.3 (s; CMe$_3$), 33.4 (dd, J(CP)=24.7, 1.9 Hz; CH$_2$P), 30.4 (d, J(CP)=32.2 Hz; CH$_2$P), 27.5 (s; Me), 27.0 (d, J(CP)=1.7 Hz; CH$_2$), 21.8 (d, J(CP)=3.1 Hz; CH$_2$). $^{31}$P {$^1$H} NMR (81.0 MHz, CD$_2$Cl$_2$, 20° C., H$_3$PO4): δ 57.1 (d, J(PP)=38.6 Hz), 44.5 (d, J(PP)=38.6 Hz).

Example 10: Synthesis of the Complex RuCl[(R,S)-Josiphos](CNN—H)) (12)

Toluene (2 ml) was added to [RuCl2(PPh3)3] (4) (0.150 g, 0.156 mmol) and (R,S)-Josiphos.C$_2$H$_5$OH (120 mg, 0.187 mmol) and the suspension was refluxed for 1 h. The solvent was removed under reduced pressure and the residue was treated with 2-propanol (2 ml), the ligand HCNN—H (1) (36 mg, 0.172 mmol) and NEt3 (0.22 ml, 1.58 mmol). The mixture was refluxed for 2 h and then cooled to room temperature. Addition of pentane (5 ml) afforded a precipitate which was filtered, washed with pentane (4×3 ml) and dried under reduced pressure. The solid was dissolved in CH$_2$Cl$_2$ (0.5 ml), kept at –20° C. for 18 h, to afford the precipitation of triethylammonium chloride which was eliminated by filtration. The solution was concentrated (1 ml) and addition of pentane (2 ml) afforded an orange precipitate which was filtered, washed with pentane (2×2 ml) and dried under reduced pressure. Yield: 90 mg (61%).

Elemental analysis (%) calculated for C$_{50}$H$_{55}$ClFeN$_2$P$_2$Ru. C, 64.00; H, 5.91: N, 2.99. Found C, 64.30; H, 6.02, N, 3.05. $^1$H NMR (200.1 MHz, CD$_2$Cl$_2$, 20° C., TMS): δ 8.33 (d, J(HH)=7.0 Hz, 1H, aromatic proton), 8.22-7.16 (m, 16H; aromatic protons), 4.70-4.35 (m, 4H; FeCH+CHP), 4.24-4.10 (m, 2H; CH$_2$N), 3.79 (s, 5H; C$_5$H$_5$), 3.45 (m, 1H, NH$_2$), 2.95-0.60 (m, 26H; CH+CH$_2$+CH$_3$+NH$_2$). $^{13}$C {$^1$H} NMR (50.3 MHz, CD$_2$Cl$_2$, 20° C.): δ 158.0-117.0 (m; aromatic carbons), 74.4 (s; FeC$_5$H$_3$), 70.8 (s; FeC$_5$H), 70.3 (d, J(CP)=-4.3 Hz; FeC$_5$H$_3$), 68.9 (d, J(CP) 4.8 Hz; FeC$_5$H$_3$), 53.0 (d, J(CP)=1.8 Hz; CHNH$_2$), 40.4 (d, J(CP)=15.8 Hz; CH of Cy), 38.0 (d, J(CP)=17.5 Hz; CH of Cy), 31.8-23.1 (m; CH$_2$ of Cy), 29.6 (d, J(CP)=3.5 Hz; PCMe), 15.9 (d, J(CP)=6.8 Hz; PCMe). $^{31}$P {$^1$H} NMR (81.0 MHz, CDCl$_3$, 20° C., H$_3$PO$_4$): δ 68.8 (d, J(PP)=42.0 Hz), 43.4 (d, J(PP)=42.0 Hz).

Example 11: Synthesis of the Complex. RuCl[(S,R)-Josiphos*](CNN—H) (13)

(Mixture of Three Diastereomers in a 1:0.06:0.20 Ratio)

The complex RuCl$_2$(PPh$_3$)$_3$ (4) (0.150 g, 0.156 mmol) was reacted for one hour with (S,R)-Josiphos* (133 mg, 0.187 mmol) in 2 ml of dichloromethane. The solvent was then eliminated and HCNN4-H (1) (36 mg, 0.172 mmol), triethylamine (0.22 ml, 1.58 mmol) and 2 ml of a 2-propanol/heptane (1:1) mixture were added. The mixture obtained was refluxed (110° C.) overnight. The solid that formed (NEt$_3$HCl) was filtered off, the solvent was eliminated, heptane (2 ml) was added and the solution obtained was maintained under reflux for 2 hours. The solution volume was then reduced to one half and 1 ml of pentane was added. The precipitate was filtered off, washed with (3×2 ml) pentane and dried under reduced pressure. The solid was suspended in dichloromethane (0.5 ml) and kept at –20° C. overnight. After filtration, the solution volume was reduced to one half and pentane was added (2 ml). The precipitate was filtered off, washed with pentane (2×2 ml) and dried under reduced pressure. Yield: 90 mg (55%).

Elemental analysis (%) calculated for C$_{56}$H$_{67}$ClFeN$_2$O$_2$P$_2$Ru: C, 63.79; H, 6.40; N, 2.66. Found C, 64.02; H, 6.60; N, 2.86. $^{31}$P {$^1$H} NMR (81.0 MHz CD$_2$Cl$_2$, 20° C., H$_3$PO$_4$): (5 67.3 (d, J(PP)=41.9 Hz), 38.5 (d, J(PP)=41.9 Hz) principal product; 60.1 (d, J(PP)=40.0 Hz), 40.9 (d, J(PP)=40.0 Hz); 64.4 (d, J(PP)=34.5 Hz), 56.1 (d, J(PP)=34.5 Hz) minor product.

Example 12: Synthesis of the Complex RuCl[(S,S)-(–)-Skewphos](CNN) (14)

(Mixture of Two Diastereomers in a 1:0.23 Ratio)

The complex RuCl$_2$(PPh$_3$)$_3$ (4) (0.150 g, 0.156 mmol) was reacted with (S,S)-(–)-Skewphos (89 mg, 0.202 mmol) in 3 ml of toluene. The suspension was refluxed for 2 hours, toluene was evaporated, and HCNN—H (1) (36 mg, 0.172 mmol), triethylamine (0.22 ml, 1.58 mmol) and 2-propanol (2 ml) were added. The mixture was then heated again under reflux (110° C.) for 2 hours. The precipitate obtained by addition of pentane was filtered off, and washed with pentane (3×3 ml). The solid was suspended in dichloromethane (0.5 ml) and kept at –20° C. overnight. After filtration, the solution volume was reduced to one half and pentane was added (2 ml). The precipitate was filtered off, washed with pentane (1×2 ml) and dried under reduced pressure. Yield: 70 mg (57%).

Elemental analysis (%) calculated for C$_{43}$H$_{41}$ClN$_2$P$_2$Ru: C, 65.85; H, 5.27, N, 3.57. Found C, 66.06, H, 5.37; N, 3.63. $^1$H NMR (200.1 MHz, CD$_2$Cl$_2$, 20° C., TMS): S 8.31-5.80 (m, 27H; aromatic protons), 4.42 (s), 4.20 (d, J(HH)=3.4 Hz), 3.68 (s broad), 3.37 (m), 3.03(m), 2.78 (s broad), 2.36 (q, J(HH)=13.5 Hz), 2.00-1.40 (m), 1.35 (t, J(HH)=7.4 Hz), 1.29 (dd, J(HP), J(HH)=14.5, 7.3 Hz), 0.91 (m broad), 0.76 (s broad), 0.55 (dd, J(HP), J(HH)=6.9, 11.4 Hz). $^{13}$C($^1$H) NMR (50.3 MHz, CD$_2$Cl$_2$, 20° C.): δ 178.5 (m; CRu), 159.3-116.2 (m; aromatic carbons), 51.3 (d, J(CP)=1.5 Hz; CH$_2$N), 37.9 (m; CH$_2$), 33.0 (m; PCH), 32.6 (m; PCH), 20.1 (s; CH3), 19.5 (d, J(CP)=6.1 Hz; CHCH$_3$), 17.5 (d, J(CP)=6.5 Hz; CHCH$_3$). $^{31}$P {$^1$H} NMR (81.0 MHz, CD$_2$Cl$_2$, 20° C., H$_3$PO$_4$): δ 66.2 (d, J(PP)=46.1 Hz), 47.8 (d, J(PP)=46.2 Hz), principal product, 64.4 (d, J(PP)=48.7 Hz), 53.3 (d, J(PP)=48.7 Hz).

Example 13: Synthesis of the Complex RuCl[(S)-MeO=Biphep](CNN—H) (15)

(Mixture of Two Diastereomers in a 1:0.18 Ratio)

The complex RuCl$_2$(PPh$_3$)$_3$ (4) (0.150 g, 0.156 mmol), and S-MeO-Biphep (136 mg, 0.233 mmol) were refluxed for 1 hour in 2 ml of toluene, after which the toluene was evaporated and HCNN—H (1) (36 mg, 0.172 mmol), triethylamine (0.22 ml, 1.58 mmol) and 2-propanol (2 ml) were added. The mixture was then heated at reflux (110° C.) for 2 hours. The precipitate obtained by addition of pentane was filtered off and washed with pentane (4×3 ml). The solid was suspended in dichloromethane (0.5 ml) and kept at −20° C. overnight. After filtration, the solution volume was reduced to one half and pentane was added (2 ml). The precipitate was filtered off, washed with pentane (2×2 ml) and dried under reduced pressure. Yield: 95 mg (66%).
Elemental analysis (%) calculated for C$_{52}$H$_{43}$ClN$_2$O$_2$P$_2$RU: C, 67.42; H, 4.68; N, 3.02. Found C, 67.93; H, 4.80; N, 3.12. $^1$H NMR (200.1 MHz, CDCl$_3$, 20° C., TMS): δ 8.45 (d, J(HH)=7.0 Hz), 8.07-5.52 (m; aromatic protons), 4.43 (dd, J(HH)=15.8, 5.4 Hz; CH$_2$), 4.25 (m), 3.88 (s; OMe), 3.74 (s; OMe), 3.39 (s; OMe), 3.28 (s; OMe), 2.05 (t, J(HH)=7.3 Hz; NH$_2$). $^{13}$C {$^1$H} NMR (50.3 MHz, CDCl$_3$, 20° C., TMS): δ 177.8 (m; CRu), 164.8-110.6 (m; aromatic carbons), 55.8 (s, OCH$_3$), 55.7 (s, OCH$_3$), 54.9 (s, OCH$_3$), 54.6 (s, OCH$_3$), 52.2 (d, J(CP)=1.7 Hz; CH$_2$). $^{31}$P {$^1$H} NMR (81.0 MHz, CD$_2$Cl$_2$, 20° C., H$_3$PO$_4$): δ 50.3 (d, J(PP)=35.5 Hz), 49.8 (d, J(PP)=35.5 Hz), principal product; 60.3 (d, J(PP)=40.5 Hz), 51.9 (d, J(PP)=40.5 Hz).

Example 14: Synthesis of the Complex OsCl[PPh$_2$(CH$_2$)$_4$PPh$_2$](CNN—H) (7a)

The complex OsCl$_2$(PPh$_3$)$_3$ (4a) (200 mg, 0.191 mmol) and bis(1,4-diphenylphosphino)butane (98 mg, 0.230 mmol) were dissolved in anhydrous CH$_2$Cl$_2$ (5 ml), to obtain a green solution which was stirred at ambient temperature for 2 hours. The solvent was evaporated under reduced pressure and the residue suspended in 2-propanol (5 ml), to which the HCNN—H ligand (1) (48 mg, 0.230 mmol) and triethylamine (0.32 ml, 2.30 mmol) were added. The mixture was then refluxed for 3 hours, to obtain a red precipitate which was filtered off, washed with 2-propanol (3×10 ml) and pentane (2×10 ml). The product was dried under reduced pressure at 45° C. overnight. Yield: 144 mg (88%).
Elemental analysis (%) calculated for C$_{42}$H$_{39}$ClN$_2$OsP$_2$: C, 58.70; H, 4.57; N, 3.26. Found: C, 58.42; H, 4.74; N, 3.27. $^1$H NMR (200.1 MHz, CD$_2$Cl$_2$, 20° C., TMS): δ 8.13 (pseudo t, J(HH)=7.5 Hz, 2H; aromatic protons), 7.93 (d, J(HH)=6.9 Hz, 1H; aromatic. proton), 7.76 (t, J(HH)=7.5 Hz, 2H; aromatic protons), 7.64-7.20 (m, 16H; aromatic protons), 6.98 (d, J(HH)=8.1 Hz, 1H; aromatic proton), 6.44 (t, J(HH)=7.3 Hz, 1H; aromatic proton), 6.17 (pseudo t, J(HH)=7.8 Hz, 2H; aromatic protons), 5.49 (t, J(HH)=7.9 Hz, 2H; aromatic protons), 4.50 (d, J(HH)=20.7 Hz, 1H; CH$_2$NH$_2$), 4.00 (m, 2H; NH$_2$, CH$_2$NH$_2$), 3.53 (m, 1H; CH$_2$), 3.30-2.65 (m, 2H; CH$_2$, NH$_2$), 2.42-1.48 (m, 6H; CH$_2$). $^{13}$C {$^1$H} NMR (50.3 MHz, CD$_2$Cl$_2$, 20° C., TMS): δ 157.2 (t, J(CP)=6.5 Hz; C—Os), 155.6 (s; NCC), 154.5 (s; NCCH$_2$), 147.7-115.8 (m; aromatic carbons), 54.6 (s; CH$_2$N), 35.2 (dd, J(CP)=36.5, 4.3 Hz; CH$_2$), 30.2 (dd, J(CP)=42.2, 5.2 Hz; CH$_2$), 26.7 (s; CH$_2$), 21.2 (t, J(CP)=2.0 Hz; CH$_2$), $^{31}$P {$^1$H} NMR (81.0 MHz, CD$_2$Cl$_2$, 20° C., H$_3$PO$_4$): δ 0.9 (d, J(PP)=13.7 Hz), 0.8 (d, J(PP)=13.7 Hz).

Example 15: Synthesis of the Complex OsH[PPh$_2$(CH$_2$)$_4$PPh$_2$](CNN—H) (8a)

A 0.1 M solution of NaO$^i$Pr (1.3 ml, 0.130 mmol) in 2-propanol was added to a suspension of complex of example 14 (7a) (100 mg, 0.116 mmol) in toluene (1.3 ml) and the mixture was stirred at 35° C. for 3 h. The resulting dark red solution was kept at −20° C. for 4 h to afford the precipitation of NaCl, which was filtered on celite (fine frit). The solvent was eliminated at low pressure and the solid was extracted with pentane (1 ml), affording a brown product which was dried under reduced pressure. Yield: 71 mg (74%).
Elemental analysis (%) calculated for C$_{42}$H$_{40}$N$_2$OsP$_2$: C, 61.15, 114.89, N, 3.40; found: C, 60.85, H, 5.02, N, 3.13. $^1$H NMR (200.1 MHz, C$_6$D$_6$, 20° C.): 5=8.53 (t, J(H,H)=8.5 Hz, 2H; aromatic protons), 8.31 (d, J(H,H)=7.9 Hz, 1H; aromatic proton), 8.05-6.62 (m, 18H; aromatic protons), 6.40 (t, J(H,H)=8.2 Hz, 1H; aromatic proton), 6.25-6.05 (m, 3H; aromatic protons), 5.49 (t, J(H,H)=7.6 Hz, 2H; aromatic protons), 4.0 (t, J(H,H)=6.9 Hz, 1H; NCH$_2$), 3.66-0.70 (m, 11H; CH$_2$, NH$_2$), −5.14 ppm (dd,$^2$J(H,P)=73.9, 23.9 Hz, 1H; OsH); $^{31}$P {$^1$H} NMR (81.0 MHz, C$_6$D$_6$, 20° C.): δ=19.9 (d, 2J(P,P)=3.7 Hz), 5.4 ppm (d, $^2$J(P,P)=3.7 Hz).

Example 16: Synthesis of the Complex Os[O—CH(p-C$_6$H$_4$F)$_2$][PPh$_2$(CH$_2$)$_4$PPh$_2$](CNN—H) (9a)

A 0.1 M solution of NaO$^i$Pr (1.6 ml, 0.160 mmol) in 2-propanol was added to a suspension of complex of example 14 (7a) (123 mg, 0.143 mmol) in toluene (1.6 ml) and the mixture was stirred at 35° C. for 3 h. The resulting dark red solution was kept at −20° C. for 4 h to afford the precipitation of NaCl, which was filtered on celite (fine frit). 4.4'-difluorobenzophenone (35 mg, 0.160 mmol) was added and the mixture was stirred at RT for 1 h. The solvent was eliminated, toluene (2 ml) was added and the mixture was kept at −20° C. for 2 h, filtered on celite and the solution was concentrated. Addition of pentane (5 ml) afforded the precipitation of a dark-yellow product which was filtered and dried under reduced pressure. Yield: 107 mg (72%).
Elemental analysis (%) calculated for C$_{55}$H$_{48}$F$_2$N$_2$OOsP$_2$: C, 63.33, H, 4.64, N, 2.69; found: C, 62.84, H, 4.72, N, 2.62. $^1$H NMR (200.1 MHz, C$_6$D$_6$, 20° C.): δ=8.18 (t, J(H,H)=7.5 Hz, 1H; aromatic proton), 8.07 (d, J(H,H)=8.3 Hz, 1H; aromatic proton), 7.93 (t, J(H,H)=7.6 Hz, 2H; aromatic protons), 7.66-6.21 (m, 26H; aromatic protons), 6.04 (dt, J(H,H) 7.6, 1.8 Hz, 2H, aromatic protons), 5.83 (d, J(H,H)=8.2 Hz, 1H, aromatic proton), 5.42 (t, J(H,H)=7.9 Hz 2H; aromatic protons), 5.28 (broad s, 1H; NH$_2$), 4.61 (rn, 1H; OCH), 3.48 (m, 1H; NCH$_2$), 3.26 (s, 2H, CH$_2$ and NH$_2$), 2.91 (pseudo t, J(H,H)=13.2 Hz, 1H; NCH$_2$), 2.42 (m, 1H; CH$_2$), 2.25 (m, 2H; CH$_2$), 1.94-0.77 ppm (m, 4H; CH$_2$); $^{13}$C {$^1$H} NMR (50.3 MHz C$_6$D$_6$, 20° C.): δ=162.4 (broad d, $^1$J(C,F)=245 Hz; C—F), 162.0 (dd, $^2$J(C,P)=7.9, 3, 7 Hz; C—Os), 156.4 (s; CCN), 155.1 (s; NCCH$_2$), 147.9-113.0 (m; aromatic carbon atoms), 79.7 (broad s; OCH), 54.0 (d, $^3$J(C,P)=2.2 Hz; NCH$_2$), 33.7 (d, $^2$J(C,P)=33.2 Hz; PCH$_2$), 30.8 (d, $^2$J(C,P)=34.4 Hz; PCH2), 26.7 (s; CH$_2$), 21.6 ppm (s; CH$_2$); $^{31}$P{$^1$H} NMR (81.0 MHz, $C_6D_6$, 20° C.). δ=1.8 (d, $^2J(P,P)$=8.2 Hz), −0.8 ppm (d, $^2J(P,P)$=8.2 Hz); $^{19}F\{^1H\}$ NMR (188.3 MHz, $C_6D_6$, 20° C.): δ=−119.4, −120.1 ppm.

13. Catalytic Tests

The ruthenium(II) and osmium(II) complexes of the present invention can be used to prepare alcohols from the corresponding ketones, by hydrogen transfer and hydrogenation reactions. In the presence of the new ruthenium and osmium based catalysts and alkali metal alkoxides, different alcohols can be obtained by reduction of cyclic ketones, linear dialkyl ketones, alkyl aryl ketones and diaryl ketones $R^6C(\!\!=\!\!O)R^7$ where $R^6$ and $R^7$ represent a saturated or unsaturated aliphatic group, or an aromatic hydrocarbon group, which can either have or not have substituent alkyl groups, substituent groups containing oxygen, halogen atoms, or a heterocyclic group.

The reduction reactions by hydrogen transfer were carried out in 2-propanol under reflux with a substrate/catalyst ratio comprised between 1 000 and 100 000 and in the presence of an alkali metal alkoxide at 2 mol % relative to the substrate. It should be noted that the acetone that forms by oxidation of the 2-propanol can be separated from the reaction mixture, by exploiting its lower boiling point relative to 2-propanol. Catalytic tests carried out at 40° C. for ruthenium complexes and at 70° C. for osmium complexes under hydrogen atmosphere at low pressure (4-5 atm) and in methanol are also provided, from which it is seen that under such conditions there is complete conversion of ketone to alcohol, thus demonstrating that these complexes are also active in hydrogenation reactions with molecular hydrogen.

B1. Catalytic Tests of Hydrogen Transfer and Hydrogenation with Non-Chiral Catalysts B1.1 Reduction of Ketones and Aldehydes by Hydrogen Transfer All the procedures were carried out under argon atmosphere using previously deaerated and distilled 2-propanol.

Example 17: Catalytic Reduction of Acetophenone in the Presence of Ruthenium(II) Complexes The acetophenone reduction process catalysed by the complex (7) is described. The same method was used with the complexes (6)-(9)-(10)-(11), the results being shown in table 1.

a) Reduction of Acetophenone Catalysed by the Complex (7)

The catalyst solution was prepared in a 10 ml Schlenk, by adding 5 ml of 2-propanol to the complex (7) (1.6 mg, 0.0021 mmol). By stirring, the complex dissolved completely over a period of a few minutes. In a second Schlenk (50 ml), 240 μl of the previously prepared solution containing the catalyst and 0.4 ml of a 0.1 M NaO$^1$Pr solution in 2-propanol were added to a solution of acetophenone (240 μl, 2 mmol) in 19 ml of 2-propanol under reflux. The start of the reaction was considered to be when the complex was added. The molar ratios of acetophenone/catalyst/NaO$^1$Pr were 20000/1/400, and the substrate concentration was 0.1 M.

b) Reduction of Acetophenone Catalysed by the Complexes (6), (9), (10), (11), (7a), (8a) and (9a).

In a similar manner to the procedure used for the complex (7), tests were carried out on the catalytic reduction of acetophenone using the complexes (6), (9), (10), (11) (0.0021 mmol) and the data are given in table 1.

Example 18: Catalytic Reduction of Linear and Cyclic Dialkyl Ketones, Alkylaryl Ketones, Diarylketones and Aldehydes in the Presence of the Complex (7)

The catalyst solution was prepared in a 10 ml Schlenk by adding 5 ml of 2-propanol to the complex (7) (1.6 mg, 0.0021 mmol). By stirring, the complex completely dissolved over a period of a few minutes.

Separately, in a second Schlenk (50 ml), 240 μl of the previously prepared solution containing the catalyst and 0.4 ml of a 0.1 M NaO$^1$Pr solution in 2-propanol were added to a ketone or aldehyde solution (2 mmol) in 19 ml of 2-propanol under reflux. The start of the reaction was considered to be when the complex was added. The molar ratios of substrate/catalyst/NaO$^1$Pr were 20000/1/400, and the substrate concentration was 0.1 M. The GC analysis data are given in table 1.

TABLE 1

Catalytic reduction of ketones and aldehydes (0.1M) to alcohols in the presence of the complexes (6), (7), (9), (10), (11). The molar ratios of ketone/complex/NaO$^1$Pr were equal to 20000/1/400. The reaction was carried out under reflux.

| Complex | Ketone | Conversion % | (min) | TOF (h$^{-1}$) |
|---|---|---|---|---|
| 6$^{[a]}$ | Acetophenone | 92 | (15) | 70 000 |
| 7 | Acetophenone | 97 | (2) | 1 200 000 |
| 7$^{[b]}$ | Acetophenone | 97 | (10) | 270 000 |
| 9 | Acetophenone | 98 | (2) | 1 400 000 |
| 10 | Acetophenone | 98 | (5) | 830 000 |
| 11 | Acetophenone | 98 | (5) | 1 080 000 |
| 7 | 5-hexen-2-one | 99 | (5) | 1 130 000 |
| 7 | Cyclohexanone | 97 | (2) | 1 160 000 |
| 7 | 3'-Methoxyacetophenone | 97 | (2) | 1 800 000 |
| 7 | 2'-Chloroacetophenone | 99 | (2) | 1 800 000 |
| 7$^{[c]}$ | Cyclohexancaldehyde | 100 | (5) | 200 000 |

$^{[a]}$The molar ratios of acetophenone/(7)/NaO$^1$Pr were equal to 5000/1/100
$^{[b]}$Reaction carried out at 60° C.
$^{[c]}$Molar ratios of aldehyde/(7)/K•zCO3 were equal to 1000/1/500

The experimental results show that with the complex (7), the reduction of linear, cyclic and aryl alkyl ketones, and aldehydes to the corresponding alcohols in 2-propanol under reflux was extremely fast and was complete within a few minutes, with substrate/catalyst ratios equal to 20000 (see text). The turnover frequency values (TOF) were between 200000 and 1800000 h$^{-1}$, depending on the steric and electronic characteristics of the substrate (table 1). Examination of the data in the literature indicates that the complex (7) is one of the most active hydrogen transfer catalysts, since previously reported systems have exhibited a TOF for acetophenone of generally less than 10000 h$^{-1}$, except for the Mathieu complex which exhibits a TOP of 90000 h$^{-1}$ (H. Yang, M Alvarez, N. Lugan, R. Mathieu, *J. Chem. Soc., Chem. Commun.* 1995, 1721). Moreover the alkoxide derivative (9) and the chloride derivatives with benzo[h]quinoline ligands containing a Me or $^1$Bu group (10) and (11), exhibit very high activity comparable to that of the derivative (7).

By way of example the synthesis of benzhydryl, an important intermediate for the preparation of antihistamines and other pharmaceutical derivatives from benzophenone, is also provided. The reaction can also be carried out starting from a more concentrated solution of acetophenone (1 M) and removing the acetone produced by distillation.

In a similar manner to the procedure used for the complex (7a), tests were carried out on the catalytic reduction of acetophenone using the complexes (8a), (9a) and the data are given in table 2.

Example 19: Catalytic Reduction of Linear and Cyclic Dialkyl Ketones, Alkylaryl Ketones and Diarylketones in the Presence of the Osmium Complex (7a)

The catalyst solution was prepared in a 10 ml Schlenk by adding 5 ml of 2-propanol to the complex (7a) (1.8 mg, 0.0021 mmol), By stirring, the complex dissolves completely over a period of a few minutes.

Separately, in a second Schlenk (50 ml), 200 µl of the previously prepared solution containing the catalyst and 0.4 ml of a 0.1 M NaO$^1$Pr solution in 2-propanol were added to a solution of ketone 2 mmol) in 19 ml of 2-propanol under reflux. The start of the reaction was considered to be when the complex was added. The molar ratios of ketone/catalyst/NaO$^1$Pr were 20000/1/400. The GC analysis data are given in table 2.

TABLE 2

Catalytic reduction of ketones (0.1M) to alcohols in the presence of the complexes (7a), (8a) and (9a). The molar ratios of ketone/complex/NaO$^1$Pr were equal to 20000/1/400. The reaction was carried out under reflux.

| Complex | Ketone | Conversion % | (min) | TOF (h$^{-1}$) |
|---|---|---|---|---|
| 7a | Acetophenone | 96 | (5) | 1 300 000 |
| 7a | Acetophenone[a] | 93 | (30) | 430 000 |
| Ha | Acetophenone | 97 | 5 | 610 000 |
| 9a | Acetophenone | 99 | 5 | 810 000 |
| 7a | 5-hexen-2-one | 97 | (10) | 300 000 |
| 7a | Cyclohexanone | 98 | (5) | 700 000 |
| 7a | 2'-Methoxyacetophenone | 99 | (2) | 1 800 000 |

[a]The molar ratios of ketone/complex/NaO$^1$Pr were equal to 100000/1/2000.

Example 20: Synthesis of Benzhydryl 1.82 g of benzophenone (10 mmol) and 98 ml of 2-propanol were added to a 100 ml flask under argon atmosphere and heated to reflux. A 0.1 M NaO$^1$Pr solution in 2-propanol (2 ml) and 400 µl of a 2-propanol solution containing the catalyst (7) (3 mg, 0.0039 mmol dissolved in 8 ml of 2-propanol) were added. The molar ratios of benzophenone/catalyst/NaO$^1$Pr were equal to 50000/1/1000. $^1$H NMR analysis of the mixture indicated that the reaction was complete after 2 hours. By evaporating the solvent, a colourless residue was obtained which was extracted with 30 ml of diethyl ether. This solution was then passed through a silica filled column to remove the catalyst and sodium alkoxide. The filtrate was treated with Na$_2$SO$_4$, filtered, and removal of the solvent led to benzhydrol which was dried under reduced pressure (10$^{-2}$ mmHg). Product isolated: 1.6 g (87% yield).

B1.2 Reduction of Ketones and Imines by Hydrogenation

All the procedures were carried out under hydrogen atmosphere, using previously deaerated and distilled methanol.

Example 21: Catalytic Reduction of Linear and Cyclic Dialkyl Ketones, Alkylaryl Ketones and Imines in the Presence of Ruthenium Complexes (7) and (9) and Osmium Complex (7a) by Hydrogenation The catalyst solution was prepared in a 10 ml Schlenk by adding 2 ml of methanol to the complex (7) (1.3 mg, 0.0017 mmol, or (9) 1.6 mg, 0.0017 mmol, or (7a) 1.5 mg, 0.0017 mmol). By stirring, the complex dissolved completely over a period of a few minutes.

Separately, in a second Schlenk (25 ml), 9.6 mg of KO$^t$Bu (0.086 mmol) and 0.5 ml of the previously prepared solution containing the catalyst were added to a previously distilled solution of ketone (4.3 mmol) in methanol (7.6 ml). The mixture was transferred into a temperature controlled reactor at 40° C. for the ruthenium and 70° C. for the osmium. Molecular hydrogen (H$_2$) was introduced at a pressure of 5 bar. The start of the reaction was considered to be when the hydrogen was added. The molar ratios of ketone/catalyst/KO$^1$Bu were 10000/1/200 and the substrate concentration was 0.5 M. The GC analysis data are given in table 3.

TABLE 3

Catalytic reduction of ketones (0.5M) to alcohols in the presence of the complexes (7), (9) and (7a). The molar ratios of ketone/complex/KO$^1$Bu were equal to 10000/1/200. Temperature = 40° C. for the ruthenium complexes (7) and (9) and 70° C. for the osmium complex (7a). H7 pressure = 5 bar, solvent = methanol.

| Complex | Ketone | Conversion % | (h) | TOF (h$^{-1}$) |
|---|---|---|---|---|
| 7 | Acetophenone | 100 | (30 min) | 31 000 |
| 7[a] | Acetophenone | 98 | (1) | 17 000 |
| 7[b] | Acetophenone | 93 | (6) | 13 000 |
| 9 | Acetophenone | 98 | (30 min) | 29 000 |
| 7[c] | 5-hexen-2-one | 95 | (1) | 14 000 |
| 7 | Cyclohexanone | 100 | (1) | 19 000 |
| 7 | 2-heptanone | 100 | (1) | 30 000 |
| 7[d] | N-benzylidenebenzenaniine | 93 | (10) | 1 400 |
| 7a | Acetophenone | 99 | (2) | 7 000 |
| 7a | 2-methylcyclohexanone | 100 | (3 h) | 5 400 |

[a]The molar ratios of ketone/complex/KO$^1$Bu were equal to 5000/1/100.
[b]The molar ratios of ketone/complex/KO$^1$Bu were equal to 50000/1/1000.
[c]From the $^1$H-NMR data no reduction at the olefin bond was observed.
[d]The molar ratios of imine/complex/KO$^1$Bu were equal to 5000/1/100.

The use of these new catalysts involves a high rate of reduction of ketones with quantitative conversion into the products within a few minutes and therefore these ruthenium complexes are ideal for the synthesis of a large number of alcohols of R$_2$CHOH type and of racemic mixtures of RR'CHOH where the R, R' groups are saturated or unsaturated linear or cyclic aliphatic groups, or aromatic hydrocarbon groups, which may either possess or not possess substituent alkyl groups, substituent groups containing oxygen, halogen atoms or pyridines. Imines can also be reduced to amines by this path.

B2. Catalytic Tests with Chiral Catalysts

B2.2 Asymmetric Reduction of Ketones by Hydrogen Transfer

All the operations were carried out under argon atmosphere, using previously distilled and deaerated 2-propanol.

Example 22: Enantioselective Reduction of Acetophenone (0.1 Nl) in the Presence of Chiral Ruthenium Complexes (12)-(13)-(14)-(15)

The procedure of enantioselective acetophenone reduction catalysed by the complex (12) is described. The same method was used with the complexes (13)-(14)-(15) and the results are given in table 4.
a) Enantioselective Reduction of Acetophenone to 1-Phenylethanol Catalysed by the Complex (12).

The catalyst solution was prepared in a 10 ml Schlenk by adding 5 ml of 2-propanol to the complex (12) (1.9 mg, 0.002 mmol). By stirring, the complex completely dissolved over a period of a few minutes.

Separately, in a second Schlenk (50 ml), 240 Al of the previously prepared solution containing the catalyst and 0.4 ml of a 0.1 M NaO$^1$Pr solution in 2-propanol were added to a solution of ketone (2 mmol) in 19 ml of 2-propanol under reflux. The start of the reaction was considered to be when the complex was added. The molar ratios of ketone/catalyst/NaO$^1$Pr were 20000/1/400, and the substrate concentration was 0.1 M. The GC analysis data are given in table 4.
b) Enantioselective Reduction of Acetophenone to 1-Phenylethanol Catalysed by the Complexes (13)-(14)-(15).

In a similar manner to the procedure used for the complex (12), tests were carried out on the catalytic reduction of acetophenone using the complexes (13)-(14)45) (0.002 mmol) and the results are given in table 4.

TABLE 4

Enantioselective reduction of ketones (0.1M) to the corresponding chiral alcohols in the presence of chiral complexes of ruthenium (12)-(13)-(14)-(15) at 60° C. The molar ratios of ketone/complex/NaO$^1$Pr were equal to 20000/1/1400.

| Complex | Ketone | Conversion % | (min) | ee % | | TOF (h$^{-1}$) |
|---|---|---|---|---|---|---|
| 12 | Acetophenone | 97 | (30) | 86 | R | 125 000 |
| 12 | 2'-Chloroacetophenone | 97 | (60) | 89 | R | 64 000 |
| 13 | Acetophenone | 98 | (40) | 96 | S | 100 000 |
| 13 | 2'-Chloroacetophenone | 98 | (40) | 97 | S | 115 000 |
| 13 | 2'--Methylacetophenone | 96 | (60) | 94 | S | 60 000 |
| 14 | Acetophenone | 95 | (30) | 73 | S | 105 000 |
| 15 | Acetophenone | 97 | (30) | 26 | R | 190 000 |

B2.2 Asymmetric Reduction of Ketones by Hydrogenation

All the procedures were carried out under hydrogen atmosphere using previously distilled and deaerated methanol and ethanol.

Example 23: Catalytic Reduction of Alkylaryl Ketones in the Presence of the Complex (13) by Hydrogenation The catalyst solution was prepared in a 10 ml Schlenk by adding 2 ml of a methanol:ethanol mixture in a 7:3 ratio (by volume) to the complex (13) (1.8 mg, 0.0017 mmol). By stirring, the complex completely dissolved over a period of a few minutes.

Separately, in a second Schlenk (25 ml), 9.6 mg of KO$^t$Bu (0.086 mmol) and 0.5 ml of the previously prepared solution containing the catalyst were added to a solution of ketone (4.3 mmol) in a methanol:ethanol mixture (7:3 by volume; 7.6 ml). The mixture was transferred into a temperature controlled reactor at 40° C. Molecular hydrogen (1-12) was introduced at 5 bar pressure. The start of the reaction was considered to be when hydrogen was added. The molar ratios of ketone/catalyst/KO$^1$Bu were 10000/1/200 and the substrate concentration was 0.5 M. The GC analysis data are given in table 5.

TABLE 5

Catalytic reduction of ketones (0.5M) to the corresponding chiral alcohols in the presence of the complex (13). The molar ratios of ketone/complex/KO$^1$Bu were equal to 10000/1/200. Temperature = 40° C. H2 pressure = 5 bar, solvent = methanol:ethanol mixture (7:3 by volume).

| Ketone | Conversion % | (h) | ee % | | TOF (h$^{-1}$) |
|---|---|---|---|---|---|
| Acetophenone | 100 | (1) | 92 | S | 15 000 |
| 2'-Chloroacetophenone | 95 | (1) | 89 | S | 15 000 |
| 3'-Methoxyacetophenone | 100 | (1) | 94 | S | 16 000 |

What is claimed is:
1. A transition metal complex of general formula [MXL$_2$L'], wherein
(a) M is Os or Ru;
(a) L' is a tridentate ligand of CNN type represented by formula (Ib)

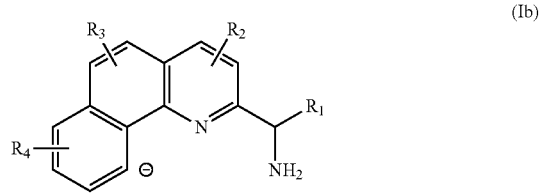

wherein R$_1$ is H, methyl, or tert-butyl and R$_2$, R$_3$, and R$_4$ are H;
(b) L is a monodentate phosphine ligand; and
(c) X is H, a halogen, or an alkoxide.
2. The transition metal complex of claim 1, wherein M is Ru.
3. The transition metal complex of claim 1, wherein L is PPh$_3$ and X is Cl.
4. The transition metal complex of claim 1, wherein R$_1$ is H.
5. The transition metal complex of claim 2, wherein L is PPh$_3$ and X is Cl.
6. The transition metal complex of claim 2, wherein L is PPh$_3$ and X is Cl and R$_1$ is H.
7. A transition metal complex of general formula [MXLL'], wherein
(a) M is Os or Ru;
(a) L' is a tridentate ligand of CNN type represented by formula (Ib)

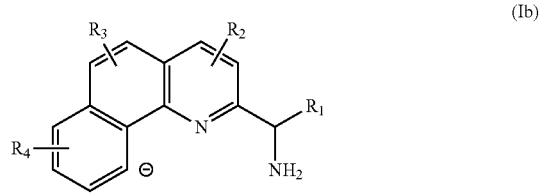

wherein R$_1$ is hydrogen, methyl, or tert-butyl and R$_2$, R$_3$, and R$_4$ are H;

(b) L is a bidentate phosphine ligand or a diphosphine ligand; and
(c) X is H, a halogen, or an alkoxide.

8. The transition metal complex of claim 7, wherein L is PPh$_2$(CH$_2$)$_4$)PPh$_2$.

9. The transition metal complex of claim 7, wherein X is Cl and R$_1$ is H.

10. The transition metal complex of claim 7, wherein X is H and R$_1$ is H.

11. The transition metal complex of claim 7, wherein X is OCH (p-C$_6$H$_4$F)$_2$ and R$_1$ is H.

12. The transition metal complex of claim 7, wherein M is Ru, X is Cl, and R$_1$ is methyl.

13. The transition metal complex of claim 7, wherein M is Ru, X is Cl, and R$_1$ is tert-butyl.

14. The transition metal complex of claim 8, wherein X is Cl and R$_1$ is H.

15. The transition metal complex of claim 8, wherein X is H and R$_1$ is H.

16. The transition metal complex of claim 8, wherein X is OCH (p-C$_6$H$_4$F)$_2$ and R$_1$ is H.

17. A transition metal complex of general formula [MXLL'], wherein
(a) M is Ru;
(a) L' is a tridentate ligand of CNN type represented by formula (Ib)

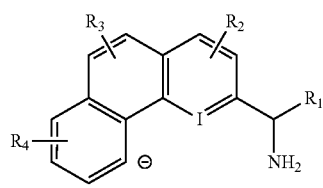

wherein R$_1$ is H, methyl, or tert-butyl and R$_2$, R$_3$, and R$_4$ are H;
(b) L is (R,S)-Josiphos; and
(c) X is Cl.

18. The transition metal complex of claim 17, wherein R$_1$ is methyl.

19. The transition metal complex of claim 17, wherein R$_1$ is tert-butyl.

20. A transition metal complex of general formula [MXLL'], wherein
(a) M is Ru;
(a) L' is a tridentate ligand of CNN type represented by formula (Ib)

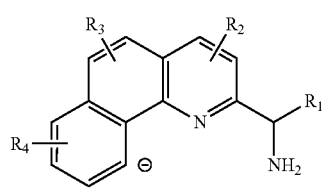

wherein R1 is H, methyl, or tert-butyl and R2, R3, and R4 are H;
(b) L is (S,R)-Josiphos*; and
(c) X is Cl.

21. The transition metal complex of claim 20, wherein R$_1$ is methyl.

22. The transition metal complex of claim 20, wherein R$_1$ is tert-butyl.

23. A transition metal complex of general formula [MXLL'], wherein
(a) M is Ru;
(a) L' is a tridentate ligand of CNN type represented by formula (Ib)

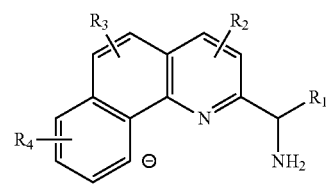

wherein R$_1$ is H, methyl, or tert-butyl and R$_2$, R$_3$, and R$_4$ are H;
(b) L is (S,S)-Skewphos; and
(c) X is Cl.

24. The transition metal complex of claim 23, wherein R$_1$ is methyl.

25. The transition metal complex of claim 23, wherein R$_1$ is tert-butyl.

26. A transition metal complex of general formula [MXLL'], wherein
(a) M is Ru;
(a) L' is a tridentate ligand of CNN type represented by formula (Ib)

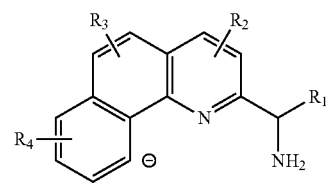

wherein R$_1$ is H, methyl, or tert-butyl and R$_2$, R$_3$, and R$_4$ are H;
(b) L is (S)-MeO-BIPHEP; and
(c) X is Cl.

27. The transition metal complex of claim 26, wherein R$_1$ is methyl.

28. The transition metal complex of claim 26, wherein R$_1$ is tert-butyl.

* * * * *